US010293110B2

(12) United States Patent
Murakami et al.

(10) Patent No.: US 10,293,110 B2
(45) Date of Patent: May 21, 2019

(54) PHARMACEUTICAL INJECTION DEVICE, METHOD FOR CONTROLLING PHARMACEUTICAL INJECTION DEVICE, PROGRAM, AND RECORDING MEDIUM

(71) Applicant: PHC Holdings Corporation, Minato-ku, Tokyo (JP)

(72) Inventors: Kenji Murakami, Ehime (JP); Mitsuteru Fujimoto, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 481 days.

(21) Appl. No.: 14/437,834

(22) PCT Filed: Nov. 22, 2013

(86) PCT No.: PCT/JP2013/006867
§ 371 (c)(1),
(2) Date: Apr. 23, 2015

(87) PCT Pub. No.: WO2014/080636
PCT Pub. Date: May 30, 2014

(65) Prior Publication Data
US 2015/0290394 A1    Oct. 15, 2015

(30) Foreign Application Priority Data
Nov. 22, 2012  (JP) .................................. 2012-256191

(51) Int. Cl.
*A61M 5/31* (2006.01)
*A61M 5/24* (2006.01)
(Continued)

(52) U.S. Cl.
CPC ............ *A61M 5/3146* (2013.01); *A61M 5/20* (2013.01); *A61M 5/24* (2013.01); *A61M 5/2448* (2013.01);
(Continued)

(58) Field of Classification Search
CPC ..... A61M 5/20; A61M 5/24; A61M 2205/581; A61M 2205/583; A61M 2205/18
See application file for complete search history.

(56) References Cited

U.S. PATENT DOCUMENTS 6,932,242 B2    8/2005    Gerlach et al.
8,298,171 B2    10/2012   Ishikawa et al.
(Continued)

FOREIGN PATENT DOCUMENTS

EP    1518575 A1    3/2005
EP    2764882 A1    8/2014
(Continued)

OTHER PUBLICATIONS

The Search Report from the corresponding International Patent Application No. PCT/PCT/JP2013/006867 dated Jan. 21, 2014.
(Continued)

*Primary Examiner* — Nathan R Price
*Assistant Examiner* — Anh T Bui
(74) *Attorney, Agent, or Firm* — Wenderoth, Lind & Ponack, L.L.P.

(57) ABSTRACT

Certain embodiments of the present invention relate to a pharmaceutical injection device, and it is an object thereof to optimize the mixing of pharmaceutical in a pharmaceutical cartridge. To achieve this object, a pharmaceutical injection device may comprise a main case, a piston, a drive motor, a buzzer, and a controller. The main case has a cartridge holder. The piston is inserted into a pharmaceutical cartridge mounted to the cartridge holder. The drive motor drives the piston. The buzzer emits a sound that tells the user to shake the pharmaceutical cartridge to mix or dissolve its contents. Before activating the drive motor and injecting the pharmaceutical, the control unit controls the buzzer so that a sound is emitted at specific intervals to prompt shaking.

20 Claims, 19 Drawing Sheets

(51) Int. Cl.
*A61M 5/20* (2006.01)
*A61M 5/315* (2006.01)

(52) U.S. Cl.
CPC ............ *A61M 2005/3125* (2013.01); *A61M 2005/31588* (2013.01); *A61M 2205/18* (2013.01); *A61M 2205/50* (2013.01); *A61M 2205/581* (2013.01); *A61M 2205/583* (2013.01)

(56) References Cited

U.S. PATENT DOCUMENTS

| | | | |
|---|---|---|---|
| 8,556,865 | B2 | 10/2013 | Krulevitch et al. |
| 8,556,866 | B2 | 10/2013 | Krulevitch et al. |
| 8,556,867 | B2 | 10/2013 | Krulevitch et al. |
| 8,679,055 | B2 | 3/2014 | Ishikawa et al. |
| 2002/0133114 | A1* | 9/2002 | Itoh .................. A61M 5/14566 604/67 |
| 2004/0057855 | A1* | 3/2004 | Gerlach ................ A61M 5/142 417/469 |
| 2005/0197650 | A1* | 9/2005 | Sugimoto ............... A61M 5/20 604/890.1 |
| 2005/0209569 | A1 | 9/2005 | Ishikawa et al. |
| 2011/0313349 | A1 | 12/2011 | Krulevitch et al. |
| 2011/0313350 | A1 | 12/2011 | Krulevitch et al. |
| 2011/0313395 | A1 | 12/2011 | Krulevitch et al. |
| 2012/0004637 | A1* | 1/2012 | Krulevitch .............. A61M 5/24 604/504 |
| 2012/0310157 | A1 | 12/2012 | Ishikawa et al. |
| 2014/0142507 | A1* | 5/2014 | Armes .................. A61M 5/422 604/112 |
| 2014/0148760 | A1 | 5/2014 | Ishikawa et al. |
| 2014/0243787 | A1 | 8/2014 | Mukai et al. |
| 2015/0051538 | A1 | 2/2015 | Hata et al. |

FOREIGN PATENT DOCUMENTS

| | | |
|---|---|---|
| EP | 2777731 A1 | 9/2014 |
| JP | 2004-024874 A | 1/2004 |
| JP | 2005-287676 A | 10/2005 |
| JP | 2009-279438 A | 12/2009 |
| JP | 2012-519028 A | 8/2012 |
| WO | 2013/069305 A | 5/2013 |

OTHER PUBLICATIONS

European Search Report from the corresponding European Patent Application No. 13856923.1 dated Dec. 7, 2015.

\* cited by examiner

PHARMACEUTICAL INJECTION DEVICE, METHOD FOR CONTROLLING PHARMACEUTICAL INJECTION DEVICE, PROGRAM, AND RECORDING MEDIUM

PRIORITY

This is a National Stage Application under 35 U.S.C. § 365 of International Application PCT/JP2013/006867, with an international filing date of Nov. 22, 2013, which claims priority to Japanese Patent Application No. 2012-256191 filed on Nov. 22, 2012. The entire disclosures of International Application PCT/JP2013/006867 and Japanese Patent Application No. 2012-256191 are hereby incorporated herein by reference.

TECHNICAL FIELD

Certain embodiments of the present invention relate to a pharmaceutical injection device for injecting insulin, growth hormones, or other such pharmaceuticals, and to a method for controlling a pharmaceutical injection device.

BACKGROUND

A conventional pharmaceutical injection device of this type was configured to comprise a needle mounting component, a main case that had a cartridge holder, a lighting component for the cartridge holder, a piston that was inserted into a pharmaceutical cartridge mounted to the cartridge holder, a drive motor for driving this piston, and a controller that was connected to this drive motor. This lighting component was used to make it easier to check the remaining amount of pharmaceutical, etc., as is introduced in the following Patent Literature 1 (Japanese Laid-Open Patent Application 2004-24874), for example.

Also, with the pharmaceuticals used in recent years, when a pharmaceutical is dissolved or mixed in a solution, for example, there are cases in which pharmaceutical and a solution are separated. Depending on the type of pharmaceutical, the pharmaceutical injection device sometimes needs to be shaken before the pharmaceutical is injected into a body, in order to mix or dissolve the pharmaceutical in the pharmaceutical cartridge mounted to the cartridge holder.

This dissolution or mixing has to be performed by the user, and a message telling the user to shake the pharmaceutical injection device to which the pharmaceutical cartridge is mounted is displayed on a display component or the like of the pharmaceutical injection device, for example.

SUMMARY

As discussed above, the user shakes the pharmaceutical injection device as instructed by a message displayed on the display component, but the shaking is not always carried out properly.

Specifically, if the timing at which the pharmaceutical injection device is shaken is too soon or too late, or if it is not shaken enough times, etc., the pharmaceutical may not be properly dissolved or mixed.

Also, although the dissolution or mixing state of the pharmaceutical in the pharmaceutical cartridge can be checked using the lighting component that is used to check how much pharmaceutical remains, this places a burden on the user because he has to check the state of the pharmaceutical repeatedly if the pharmaceutical is not properly dissolved or mixed due to an improper shaking operation.

In view of this, and taking into account the above-mentioned problems encountered with conventional pharmaceutical injection devices, it is an object of certain embodiments of the present invention to provide a pharmaceutical injection device, and a method for controlling a pharmaceutical injection device, with which a pharmaceutical can be dissolved or mixed more properly.

In one aspect of this disclosure, a pharmaceutical injection device comprises a main case, a piston, a drive motor, an instruction signal generator, and a controller. The main case has a cartridge holder. The piston is inserted into a pharmaceutical cartridge mounted to the cartridge holder. The drive motor drives the piston. The instruction signal generator generates an instruction signal that instructs the user to shake the pharmaceutical cartridge to mix or dissolve the pharmaceutical it contains.

The controller controls the instruction signal generator so as to issue the instruction signal at specific intervals to give an instruction to shake, before the drive motor is actuated to inject the pharmaceutical.

Because the configuration is such that an instruction signal is generated at specific intervals prior to pharmaceutical injection, the pharmaceutical in the pharmaceutical cartridge mounted to the cartridge holder can be more properly dissolved or mixed by shaking the main case as directed by this instruction signal.

The pharmaceutical injection device pertaining to another aspect of the present invention comprises a main case, a holder lighting component, a piston, a drive motor, an acceleration sensor, and a controller. The main case has a cartridge holder. The holder lighting component illuminates the cartridge holder. The piston is inserted into a pharmaceutical cartridge mounted to the cartridge holder. The drive motor drives the piston. The acceleration sensor is connected to the main case. The controller lights the holder lighting component when the number of shakes sensed by the acceleration sensor reaches a specific number.

Thus, the number of shakes can be sensed automatically, and when the shaking is finished, the state of the pharmaceutical cartridge can be visually checked in a state in which the holder lighting component is lit, so the pharmaceutical can be injected in a more reliable mixing state.

The pharmaceutical injection device pertaining to another aspect of this disclosure comprises a main case, a piston, a drive motor, a confirmation signal generator, an acceleration sensor, and a controller. The main case has a cartridge holder. The piston is inserted into a pharmaceutical cartridge mounted to the cartridge holder. The drive motor drives the piston. The confirmation signal generator confirms whether or not shaking has been performed properly to mix or dissolve the pharmaceutical in the pharmaceutical cartridge. The acceleration sensor senses the acceleration of the main case. The controller controls the confirmation signal generator so as to generate a confirmation signal when the shaking operation is proper, on the basis of the sensing value of the acceleration sensor.

This allows the shaking operation to be performed while checking whether or not it is being done properly, so the pharmaceutical can be dissolved or mixed more properly.

The method for controlling a pharmaceutical injection device pertaining to another aspect of this disclosure is a method for controlling a pharmaceutical injection device having a cartridge holder, said method comprising a shaking instruction step. In this shaking instruction step, an instruction signal instructing the user to shake the pharmaceutical in a pharmaceutical cartridge mounted to the cartridge holder in order to mix or dissolve it prior to the injection of the pharmaceutical is issued at specific intervals so as to prompt a shaking operation.

Since an instruction signal is thus generated at specific intervals prior to pharmaceutical injection, the pharmaceutical in the pharmaceutical cartridge mounted to the cartridge holder can be more properly dissolved or mixed by shaking the main case as directed by this instruction signal.

Certain embodiments provide a pharmaceutical injection device, and a method for controlling a pharmaceutical injection device, with which a pharmaceutical can be dissolved or mixed more properly.

DETAILED DESCRIPTION

Embodiments of the present invention will now be described in detail through reference to the drawings.

Figure 1:
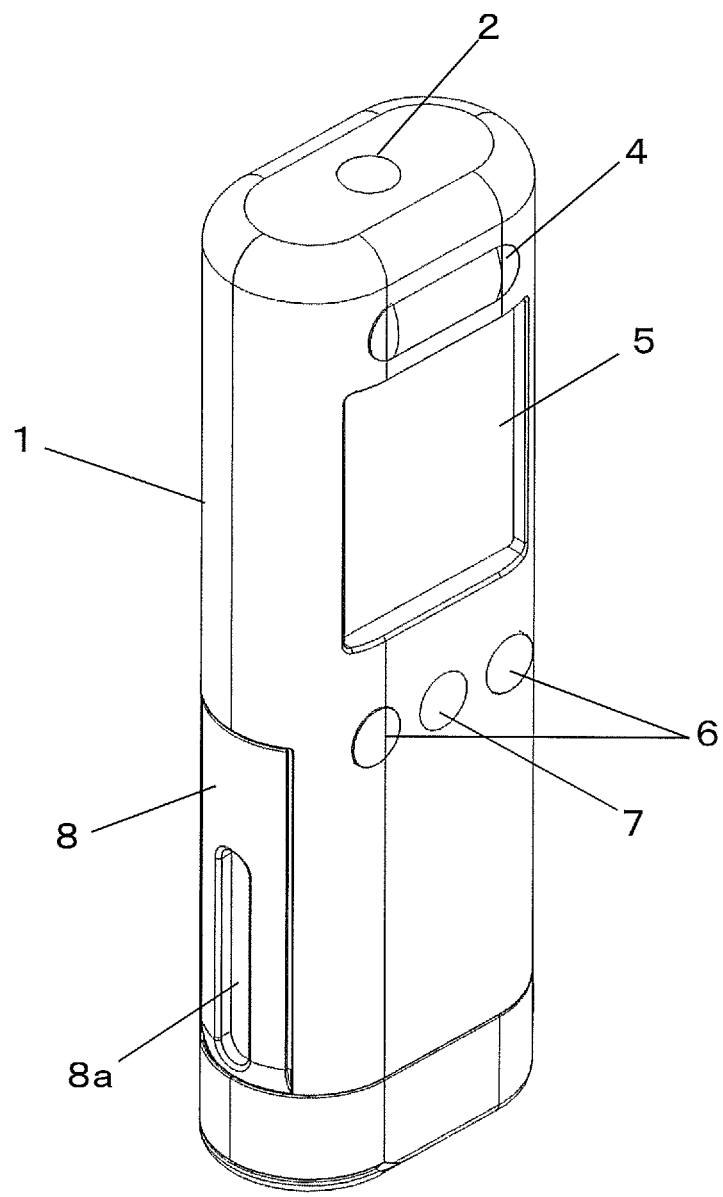
FIG. 1 is an oblique view of the pharmaceutical injection device in Embodiment 1 of the present invention.
Figure 2:
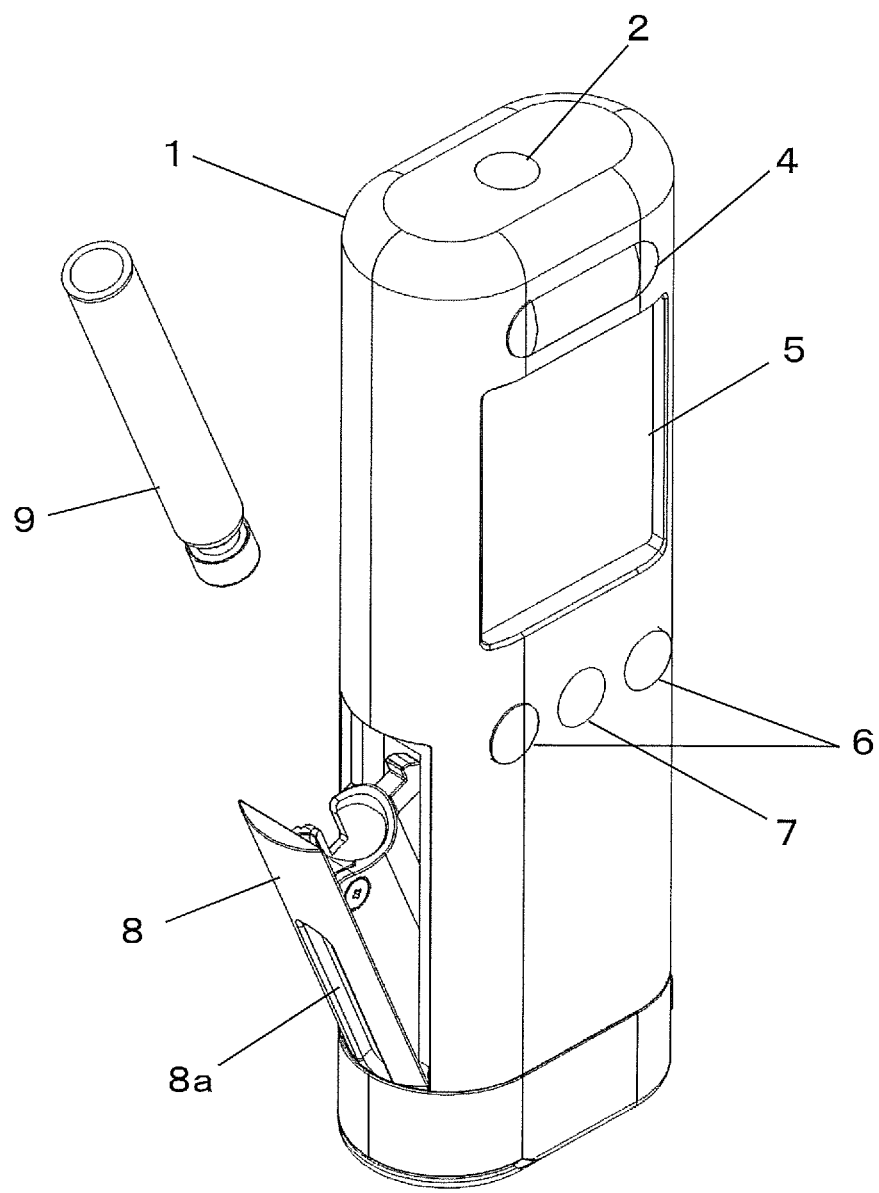
FIG. 2 is an oblique view of the state when the cartridge holder of the pharmaceutical injection device in FIG. 1 has been opened.
Figure 3:
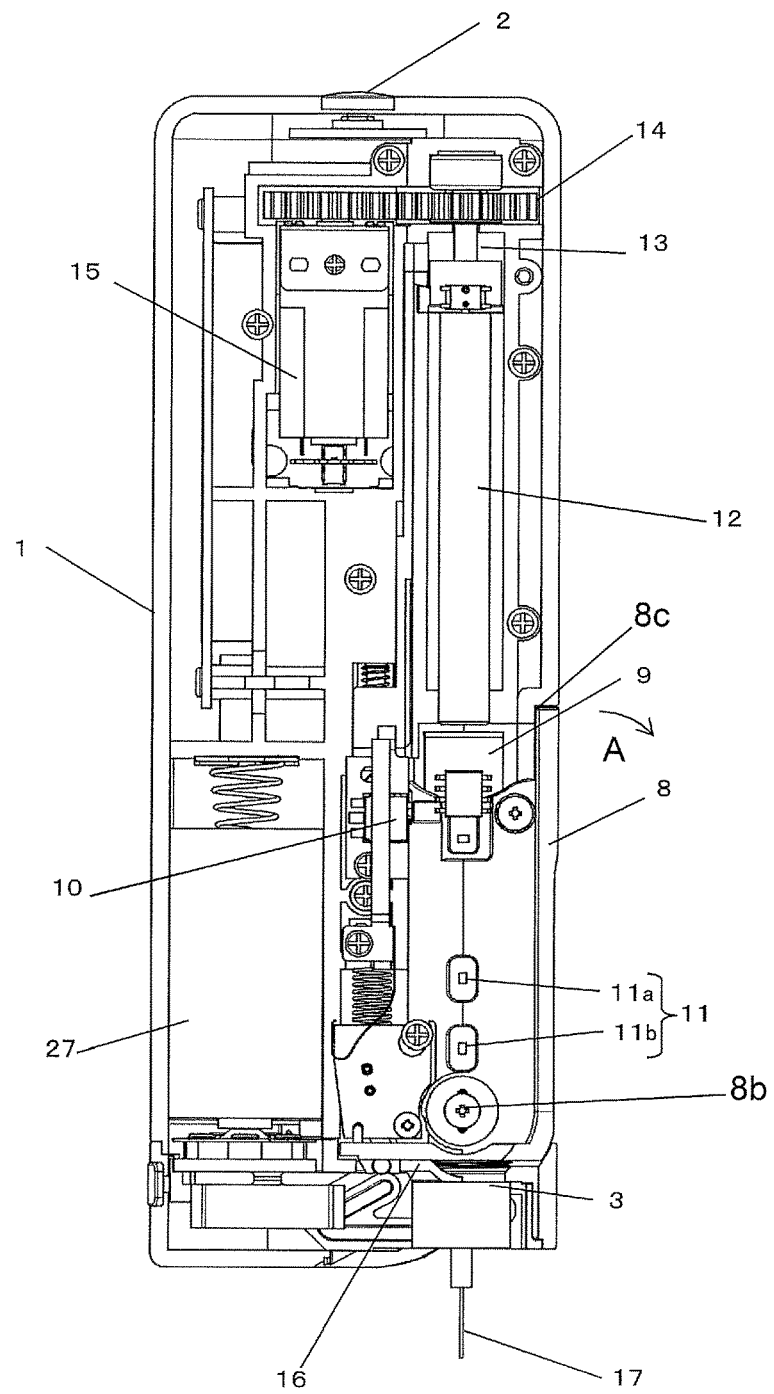
FIG. 3 is a lateral cross section of the internal configuration of the pharmaceutical injection device in FIG. 1.

FIG. 1 is an oblique view of the pharmaceutical injection device in this embodiment. FIG. 2 is an oblique view of the state when the cartridge holder of the pharmaceutical injection device in FIG. 1 has been opened. FIG. 3 is a lateral cross section of the internal configuration of the pharmaceutical injection device in FIG. 1.

As shown in FIGS. 1 and 2, the pharmaceutical injection device in this embodiment is equipped with a substantially cylindrical main case 1. A power switch 2 is connected to the upper face of this main case 1, and a needle mounting component 3 is provided as shown in FIG. 3 to the lower face. In this Specification, for the sake of description, the side on which the power switch 2 is provided will be called the top, and the side on which the needle mounting component 3 is provided (the opposite side) will be called the bottom.

A pharmaceutical injection switch 4, a display component 5, a selector switch 6, and a confirmation switch 7 are connected to the surface portion of the main case 1, from top to bottom.

As shown in FIGS. 1 and 2, the main case 1 is also provided with a cartridge holder 8 that can be opened and closed. As shown in FIG. 2, the cartridge holder 8 is configured to be able to rotate around its lower side so that its upper side opens outward. To describe this through reference to FIG. 3, the cartridge holder 8 has a rotary shaft 8b on its lower side (the needle mounting component 3 side), and the end 8c of its upper side (the power button 2 side) opens outward around this rotary shaft 8b (see the arrow A).

That is, the cartridge holder 8 is first opened as shown in FIG. 2, and then a pharmaceutical cartridge 9 is inserted into the cartridge holder 8, after which the cartridge holder 8 is closed as shown in FIG. 1, so that the pharmaceutical cartridge 9 is housed inside the main case 1 as shown in FIG. 3. Also, a cartridge detector switch 10 is connected to detect whether or not the cartridge holder 8 has been closed and the pharmaceutical cartridge 9 has been installed. The cartridge detector switch 10 is a push-type detector switch, for example, and is disposed near the upper end of the cartridge holder 8 as shown in FIG. 3. When the cartridge holder 8 is closed in a state in which the pharmaceutical cartridge 9 has been mounted, the side face part of the pharmaceutical cartridge 9 pushes the cartridge detector switch 10 and switches on, whereupon it is detected that the pharmaceutical cartridge 9 has been mounted.

Figure 4:
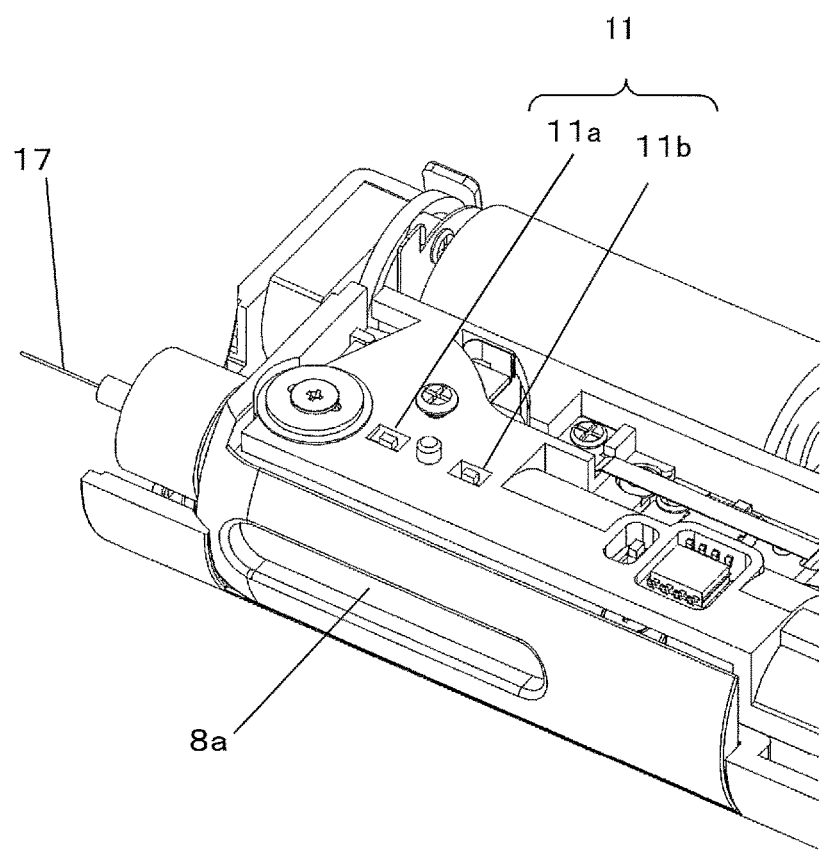
FIG. 4 is an oblique detail view of the cartridge holder and its surroundings in the pharmaceutical injection device in FIG. 1.
Figure 5:
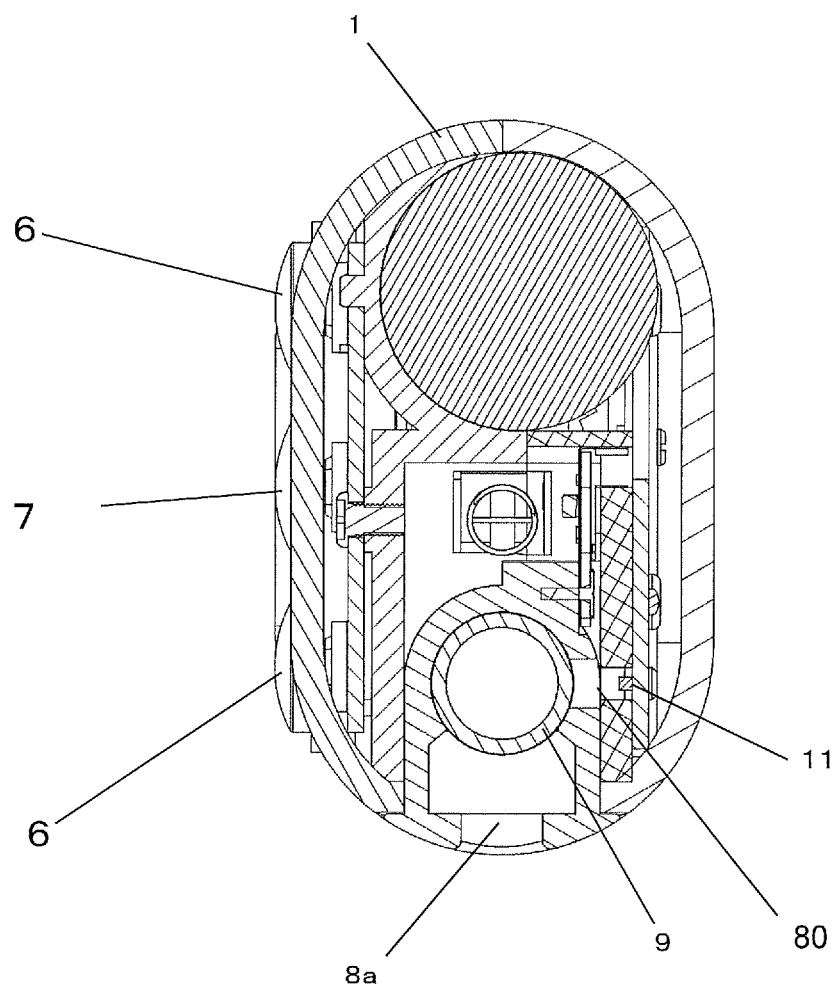
FIG. 5 is a longitudinal cross section of the state when the pharmaceutical cartridge of the pharmaceutical injection device in FIG. 1 has been mounted.

As shown in FIGS. 3 to 5, the pharmaceutical injection device in this embodiment is provided with a holder lighting component 11 that illuminates the pharmaceutical cartridge 9 mounted to the cartridge holder 8. FIG. 4 is an oblique detail view of the cartridge holder and its surroundings in the pharmaceutical injection device in this embodiment, and FIG. 5 is a longitudinal cross section of the state when the pharmaceutical cartridge to the pharmaceutical injection device in this embodiment has been mounted.

Also, a confirmation window 8a is connected to the portion of the cartridge holder 8 that corresponds to the outer surface of the main case 1 in order to confirm the state of illumination of the pharmaceutical cartridge 9.

As shown in FIG. 5, the holder lighting component 11 is disposed on the rear face side of the cartridge holder 8. Also, an opening 80 is formed on the rear face side of the cartridge holder 8. Light from the holder lighting component 11 goes through this opening 80 and shines on the pharmaceutical cartridge 9.

In this state, it can be confirmed that the pharmaceutical cartridge 9 is mounted inside, from the outside of the pharmaceutical injection device, through the confirmation window 8a.

In the example in FIG. 5, the positional relation between the holder lighting component 11 and the confirmation window 8a is such that they are disposed at positions at a 90-degree angle to the center of the pharmaceutical cartridge 9.

Also, as shown in FIG. 5, in this embodiment the holder lighting component 11 has two lights 11a and 11b.

As shown in FIG. 3, a piston 12 that is inserted to the lower part from the upper part in FIG. 3 is connected to the pharmaceutical cartridge 9 mounted in the main case 1.

The piston 12 is designed to be driven by a drive motor 15 via a gear 14 and a piston feed screw 13.

As shown in FIG. 3, a needle detector switch 16 is connected to the needle mounting component 3, and when a needle 17 is mounted to the needle mounting component 3 as shown in FIG. 3, this is detected by the needle detector switch 16.

Figure 6:
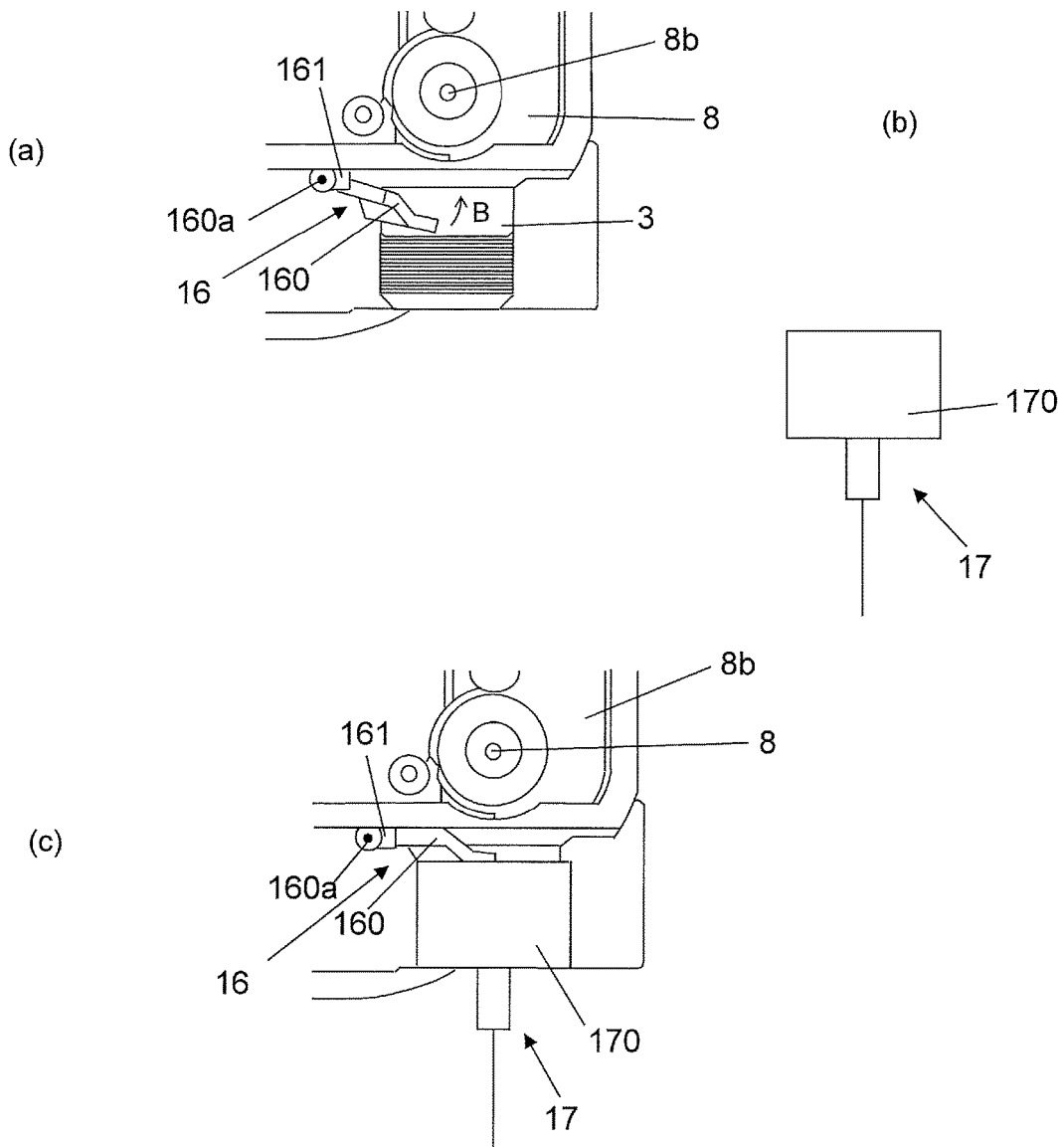
FIG. 6a shows the configuration near a needle detecting switch in a state in which a needle has not been mounted in the pharmaceutical injection device in FIG. 1.
FIG. 6b shows the configuration of the needle in FIG. 1.
FIG. 6c shows the configuration near the needle detecting switch in a state in which the needle has been mounted in the pharmaceutical injection device in FIG. 1.

FIG. 6a shows the configuration near the needle mounting component 3 in a state in which the needle 17 has not been mounted.

As shown in FIG. 6a, the needle detector switch 16 is disposed near the needle mounting component 3. The needle detector switch 16 has a rotary part 160 and a detector part 161. The rotary part 160 is configured to be able to rotate around a rotary shaft 160a, and is biased downward by a spring member or the like (not shown). The detector part 161 is switched on by upward rotation of the rotary part 160 (see the arrow B), and the mounting of the needle 17 to the needle mounting component 3 is thereby detected.

FIG. 6b shows the configuration of the needle 17. As shown in FIG. 6b, the needle 17 has a cap 170 for mounting to the needle mounting component 3. This cap 170 is cylindrical in shape, and its inside is formed in a spiral shape. Meanwhile, a spiral shape is also formed on the outside of the needle mounting component 3, and the needle 17 is mounted to the needle mounting component 3 by meshing this spiral shape with the spiral shape of the cap 170.

FIG. 6c shows the configuration near the needle mounting component 3 in a state in which the needle 17 has been mounted. As shown in FIGS. 6a to 6c, when the needle 17 is mounted, the rotary part 160 is pushed upward by the cap 170 and rotates upward around the rotary shaft 160a. This rotation switches on the detector part 161, and it is detected that the needle 17 has been mounted.

Figure 7:
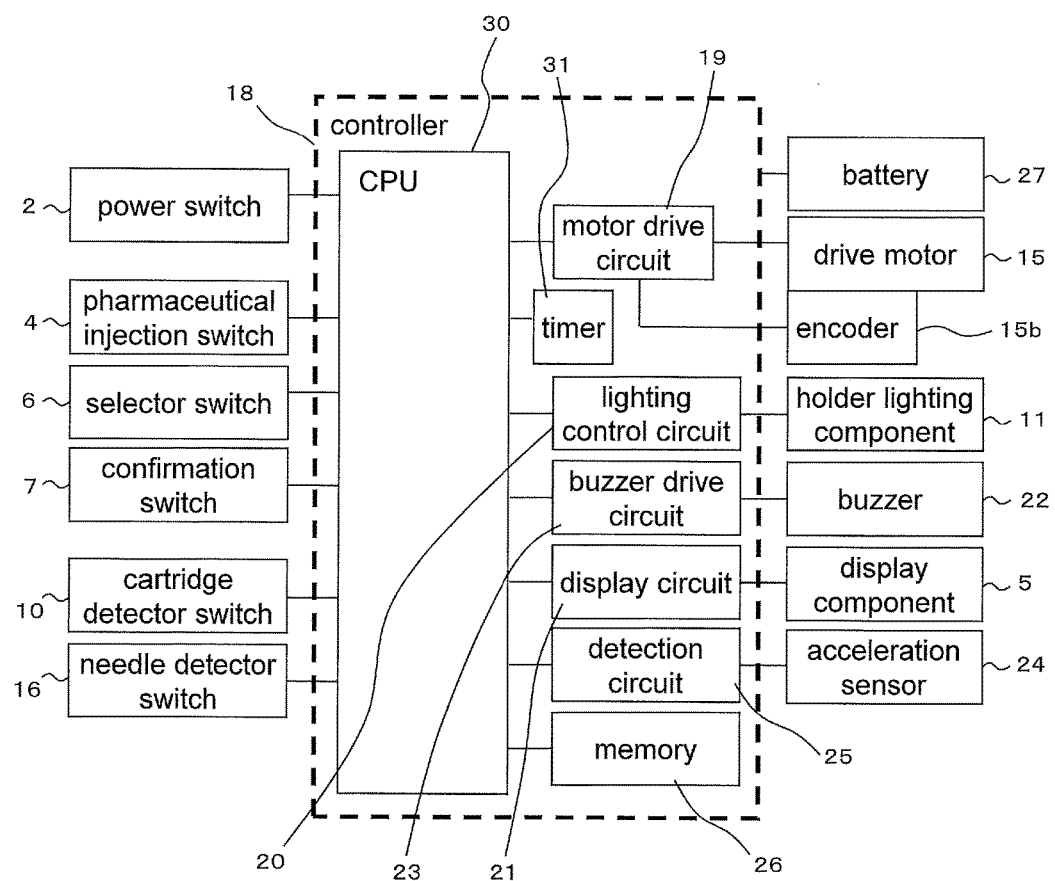
FIG. 7 is a block diagram of the configuration of the pharmaceutical injection device in FIG. 1.

FIG. 7 is a control block diagram of the pharmaceutical injection device.

The power switch 2, the pharmaceutical injection switch 4, the display component 5, the selector switch 6, the confirmation switch 7 (see FIG. 1 or 2), the cartridge detector switch 10, the holder lighting component 11, the drive motor 15, an encoder 15b, the needle detector switch 16, a buzzer 22, an acceleration sensor 24, and a battery 27 are connected to a controller 18 as shown in the control block diagram of FIG. 7.

The drive motor 15 is connected to a CPU 30 via a motor drive circuit 19 inside the controller 18. Then, the holder lighting component 11 is connected to the CPU 30 via a lighting control circuit 20 inside the controller 18.

LED lighting, a small lamp, or the like can be used for the holder lighting component 11 here, and the lighting control circuit 20 will correspondingly be an LED control circuit or a lamp control circuit, respectively.

Next, the display component 5 is connected to the CPU 30 via a display circuit 21 inside the controller 18. An LCD (liquid crystal) panel, an organic electroluminenescense panel, or the like can be used for the display component 5.

Furthermore, the buzzer 22 (an example of an instruction signal generator) is connected to the CPU 30 via a buzzer drive circuit 23 inside the controller 18. Naturally, the buzzer 22 may instead be a sounder or a speaker that outputs music, voice, or the like. If a sounder or speaker is used, the device will have a sounder drive circuit or a speech synthesis circuit, respectively. The buzzer 22 is usually disposed on a substrate, but may be disposed on the outer surface of the main case 1 or nearby.

The acceleration sensor 24 disposed in the main case 1 is connected to the CPU 30 via a detection circuit 25 inside the controller 18. The acceleration sensor 24 can be a piezo resistive type or the like, and in this embodiment it is disposed on a substrate.

A memory 26 is connected to hold operating programs, setting data, and the like. Further, the battery 27 is connected to supply power to the entire device. This battery 27 may be a dry cell or other such primary battery, or may be a secondary battery of nickel hydrogen, lithium ions, or the like. The controller 18 is provided with a timer 31 that is connected to the CPU 30, and allows time to be measured.

Figure 8:
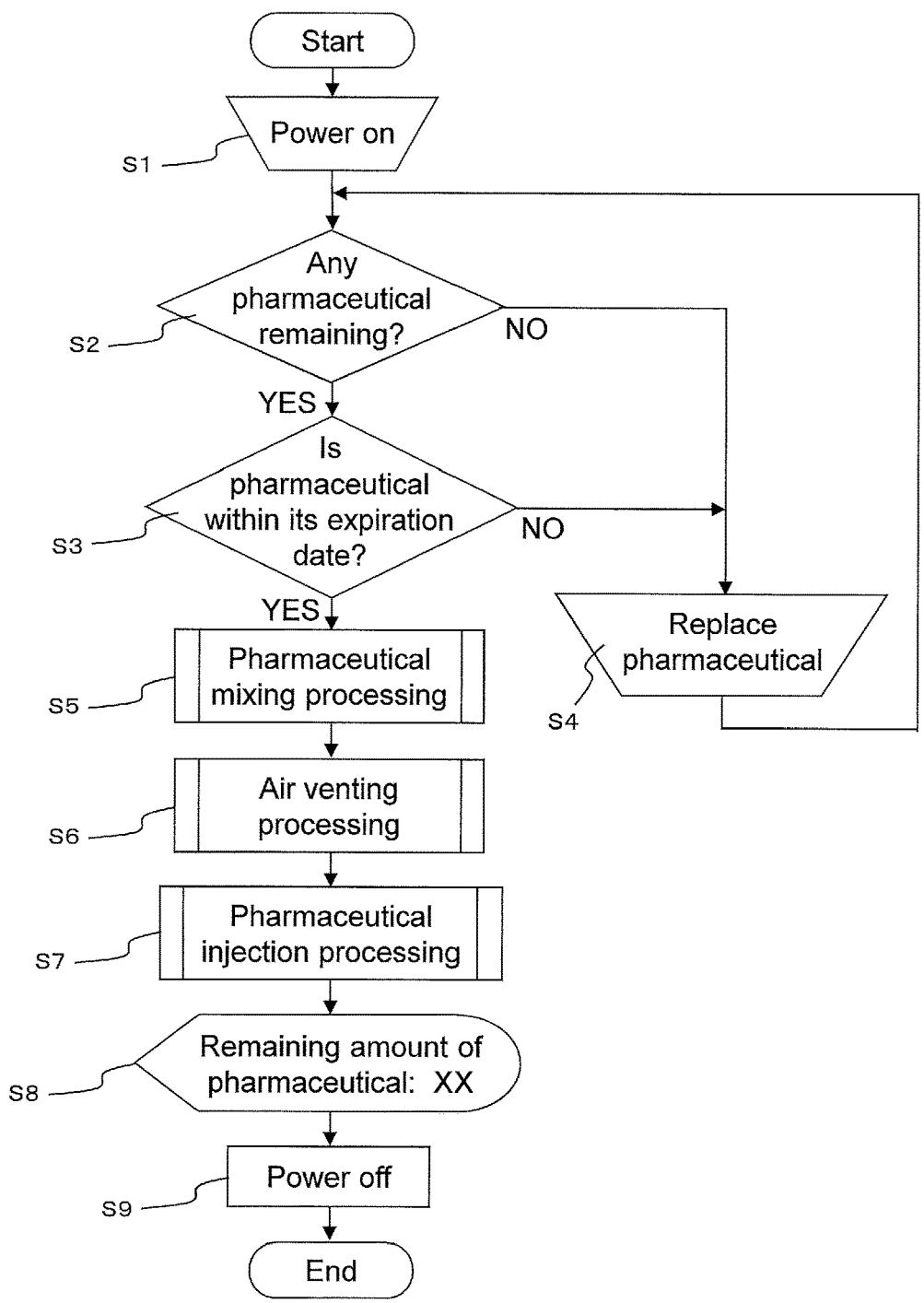
FIG. 8 is a flowchart summarizing the overall operation of the pharmaceutical injection device in FIG. 1.

Next, the operation of the pharmaceutical injection device in this embodiment will be described, and an example of the method for controlling the pharmaceutical injection device will be discussed. FIG. 8 is flowchart of the overall operation of the pharmaceutical injection device in this embodiment.

First, when the power switch 2 is operated (S1), the controller 18 checks the amount of pharmaceutical remaining (S2), and checks whether the pharmaceutical is within its expiration date (S3). More precisely, for example, the controller 18 records the date and time the pharmaceutical cartridge was last replaced, the number of pharmaceutical injections, the amount of pharmaceutical injected, and so forth in the memory 26, and determines whether the pharmaceutical is expired based on what has been recorded. If there is not enough pharmaceutical, or if the pharmaceutical has reached its expiration date, the control moves on to S4, and the pharmaceutical cartridge 9 is replaced by the user. At this point a message prompting the user to replace the pharmaceutical may be displayed on the display component 5.

In S2 and S3, if there is enough pharmaceutical remaining in the pharmaceutical cartridge 9, and the pharmaceutical is within its expiration data, pharmaceutical mixing processing is carried out (S5).

Then, once the pharmaceutical has been properly mixed and the pharmaceutical mixing processing is finished, air venting processing is carried out (S6).

Once the air venting processing is finished, pharmaceutical injection processing (S7) is then carried out, and the remaining amount of pharmaceutical is displayed (S8).

The power is then switched off, and the operation of the pharmaceutical injection device is concluded (S9).

The various operations will now be described in detail.

Figure 9:
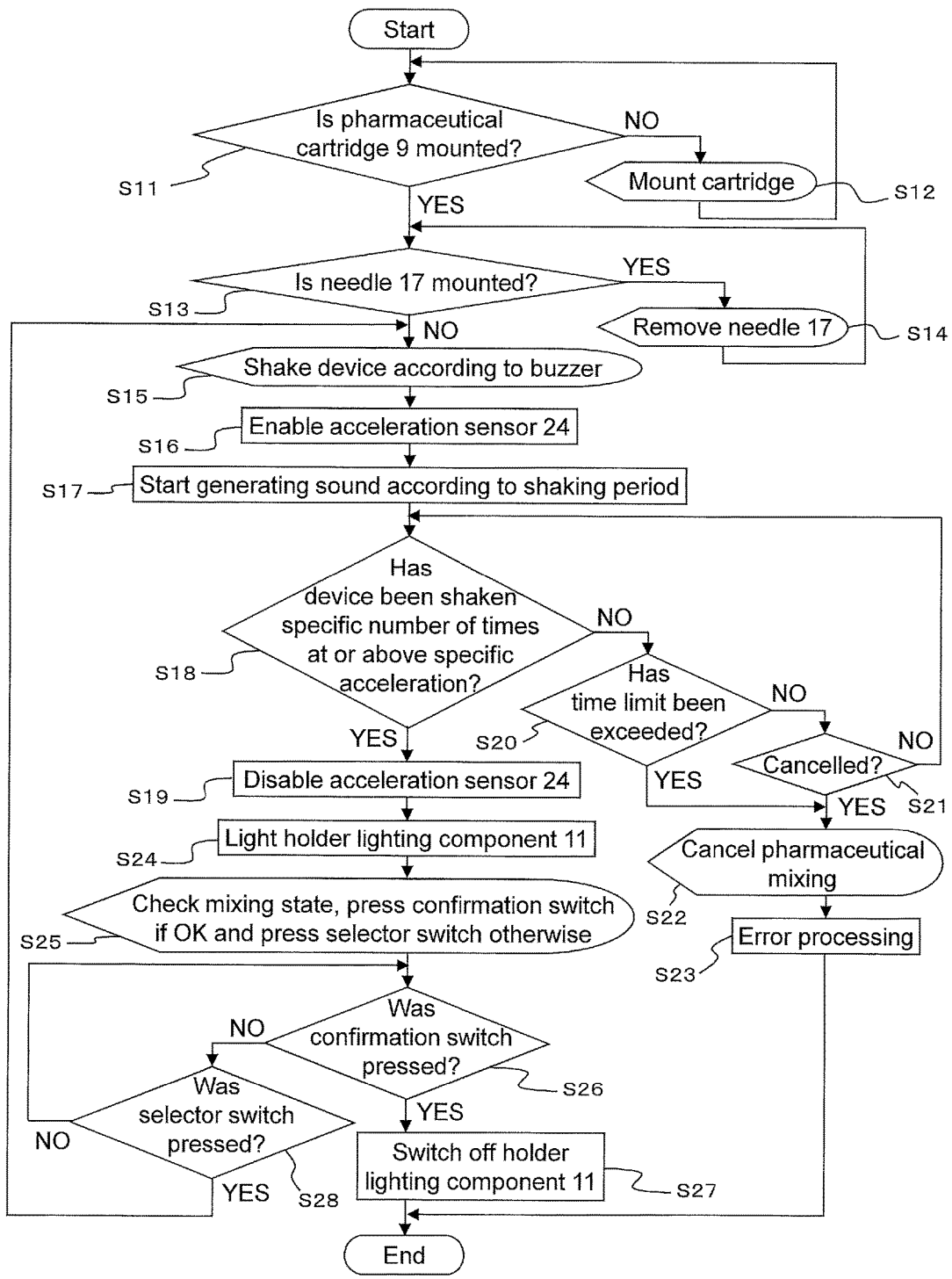
FIG. 9 is a flowchart of the pharmaceutical mixing processing in the pharmaceutical injection device in FIG. 1.

Next, pharmaceutical mixing processing (S5) will be described in detail. FIG. 9 is a flowchart of the operation in pharmaceutical mixing processing in this embodiment.

In pharmaceutical mixing processing, first the cartridge detector switch 10 is used to determine whether or not the pharmaceutical cartridge 9 has been mounted to the cartridge holder 8 (S11).

If the controller 18 determines that the pharmaceutical cartridge 9 has not been mounted to the cartridge holder 8, then the controller 18 causes the display component 5 to display an instruction to "Mount (pharmaceutical) cartridge" (S12).

If the controller 18 determines via the cartridge detector switch 10 that the pharmaceutical cartridge 9 has been mounted to the cartridge holder 8, then the controller 18 determines with the needle detector switch 16 whether or not the needle 17 has been mounted to the needle mounting component 3 (S13). This S13 corresponds to an example of the needle detection step.

If it is determined using the needle detector switch 16 that the needle 17 has been mounted to the needle mounting component 3, the controller 18 causes the display component 5 to display an instruction to "Remove needle" (S14).

That is, the pharmaceutical contained in the pharmaceutical cartridge 9 used in this embodiment is the product of mixing or dissolving a pharmaceutical in a solution, and if allowed to stand for an extended period (such as several hours), it will separate into pharmaceutical and solution. Accordingly, the main case 1 must be shaken prior to pharmaceutical injection in order to eliminate any separation of pharmaceutical and solution (to thoroughly mix them).

The main case 1 thus needs to be shaken prior to injection of the pharmaceutical, and an instruction to remove the needle 17 is given in order to avoid injury by the needle 17 during shaking (for the sake of safety).

In addition to being a safety precaution, removing the needle 17 also serves to prevent the pharmaceutical (solution) inside the pharmaceutical cartridge 9 from splashing out through the needle 17 during the shaking of the main case 1.

In S13, if it is determined that the needle 17 is not mounted to the needle mounting component 3, the controller 18 causes the display component 5 to display an instruction to "Shake device according to buzzer" (S15). This S15 corresponds to an example of the shaking instruction display step.

The controller 18 then enables input from the acceleration sensor 24 (S16).

The controller 18 then controls the buzzer 22 to generate a sound at specific intervals (that is, according to the recommended shaking period) (S17). The buzzer 22 can be any device that can generate sounds such as beeps or buzzes. This S17 corresponds to an example of the shaking instruction step.

The user checks the instruction on the display component 5 to "Shake device according to buzzer," and therefore shakes the main case 1 according to the sounds emitted from the buzzer 22.

The shaking state of the main case 1 is monitored by the acceleration sensor 24, and the controller 18 determines whether or not the main case has been shaken properly on the basis of the numerical value sensed by the acceleration sensor 24. Specifically, when the main case 1 is shaken a set number of times (such as ten times) under specific conditions (these will be discussed in detail below, but are conditions such as acceleration over a set threshold) (that is, when the number of times the main case 1 has been shaken reaches a specific number), the dissolution or mixing state of the pharmaceutical contained in the pharmaceutical cartridge 9 will be the proper state, so the generation of sounds by the buzzer 22 is continued until this state is reached (S18). That is, the buzzer 22 stops producing sounds when the number of shakes reaches a specific number. The determination of the shaking state in S18 will be described in detail below through reference to FIG. 10.

Once this state is attained, the controller 18 disables input from the acceleration sensor 24 (S19).

Meanwhile, if the specific number of shakes at the specified acceleration or higher has not been reached by the time a time limit is up (S20), or if cancel is selected from a menu display (S21), a display of "Cancel pharmaceutical mixing" is given (S22). In step S23, control is ended after error processing has been performed.

In the above-mentioned S19, after input from the acceleration sensor 24 is disabled, the controller 18 puts the holder lighting component 11 in a continuously flashing state (S24). This S24 corresponds to an example of an illumination step.

After this, the controller 18 causes the display component 5 to display an instruction of "Check mixing state and press confirmation switch if OK or selector switch if not OK" (S25). This S25 corresponds to an example of a confirmation instruction step.

That is, when the holder lighting component 11 is put in a continuously flashing state, the user can be guided to visually check the state of the pharmaceutical cartridge 9 in the cartridge holder 8 through the confirmation window 8a.

If the main case 1 is shaken in a state in which the shakes are adequately sensed by the acceleration sensor 24 according to the generation of sounds by the buzzer 22 as in this embodiment, then the pharmaceutical in the pharmaceutical cartridge 9 will be in the proper mixing state, and if the state of the pharmaceutical cartridge 9 is then visually checked through the confirmation window 8a while the holder lighting component 11 is flashing, the pharmaceutical can be injected in a more reliably state of mixing.

Therefore, if the user checks the mixing state of the pharmaceutical in the pharmaceutical cartridge 9 through the confirmation window 8a, and confirms that there is nothing wrong, the user then presses the confirmation switch 7 to advance the control (S26).

The controller 18 then switches off the holder lighting component 11, and control over pharmaceutical mixing processing ends.

On the other hand, if the user checks the mixing state of the pharmaceutical on the basis of the display in S25, and if the mixing is determined to be inadequate, the selector switch 6 is operated (S28). In this case, the control moves to S15, and the mixing operation is performed again.

The above operation allows the pharmaceutical in the pharmaceutical cartridge 9 to be properly mixed.

The determination of the shaking state performed in above-mentioned S18 will now be described in detail.

Figure 10:
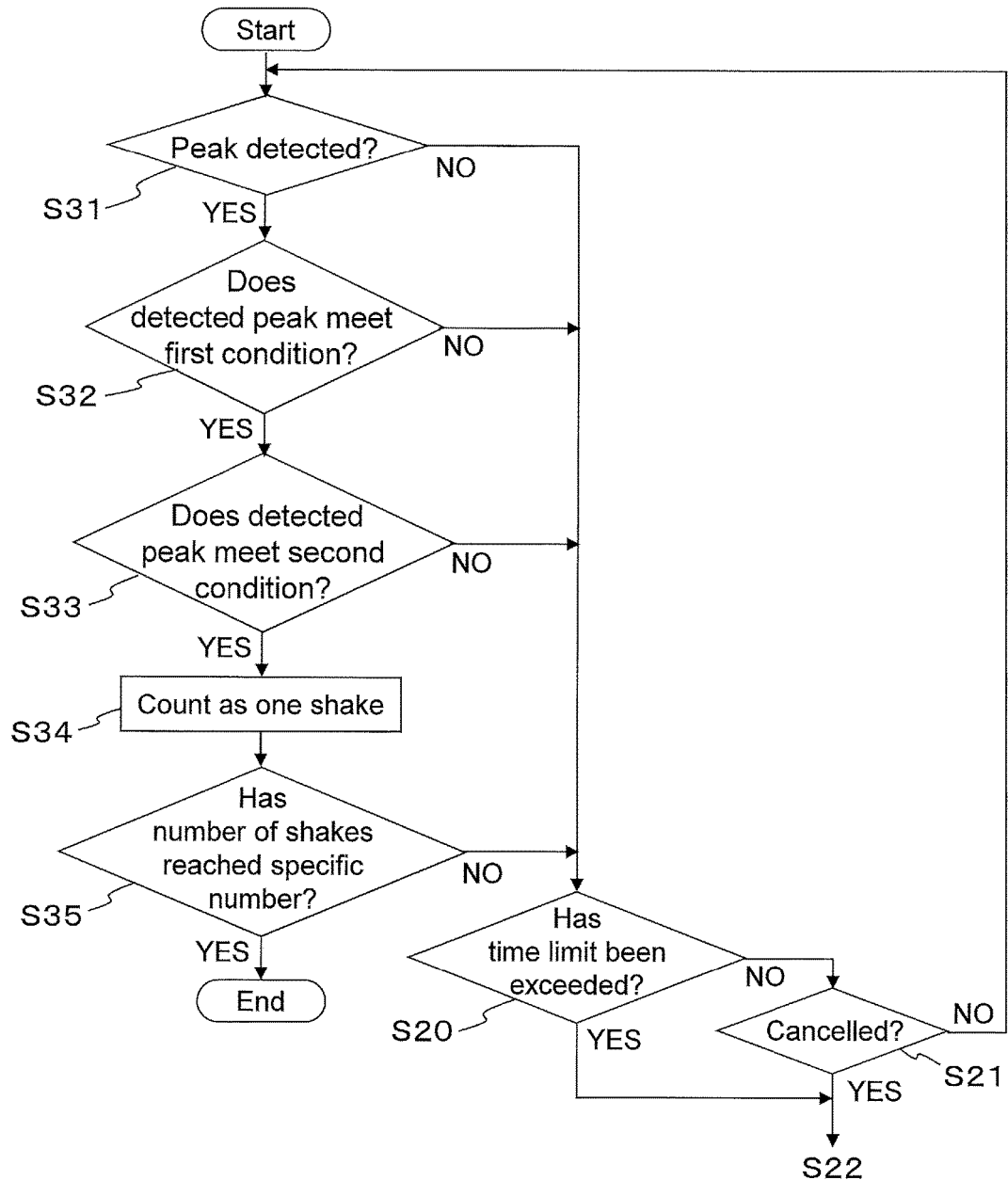
FIG. 10 is a flowchart of the shaking determination operation in the pharmaceutical injection device in FIG. 1.
Figure 11:
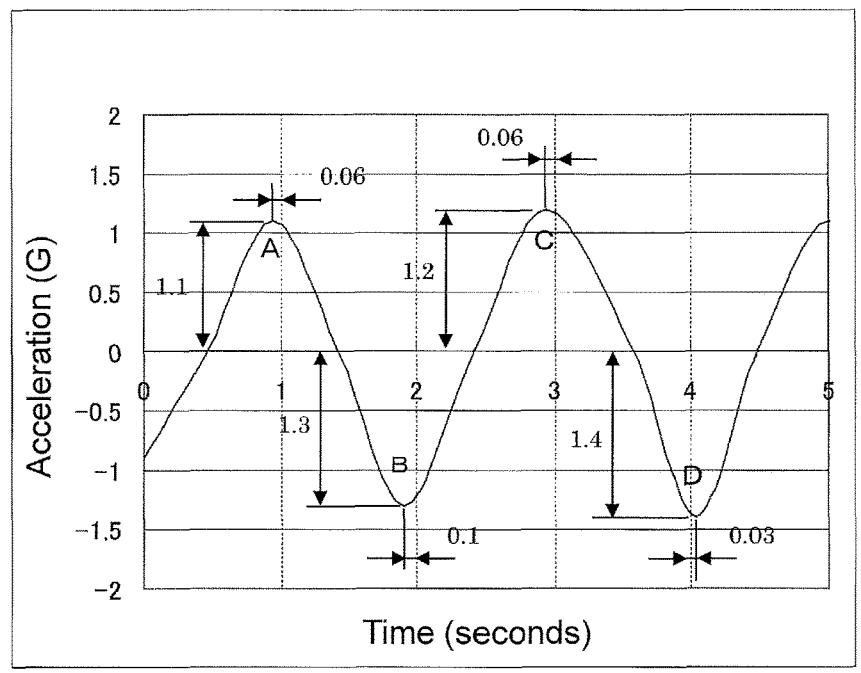
FIGS. 11a and 11b are graphs illustrating the shaking determination operation in the pharmaceutical injection device in FIG. 1.
Figure 11:
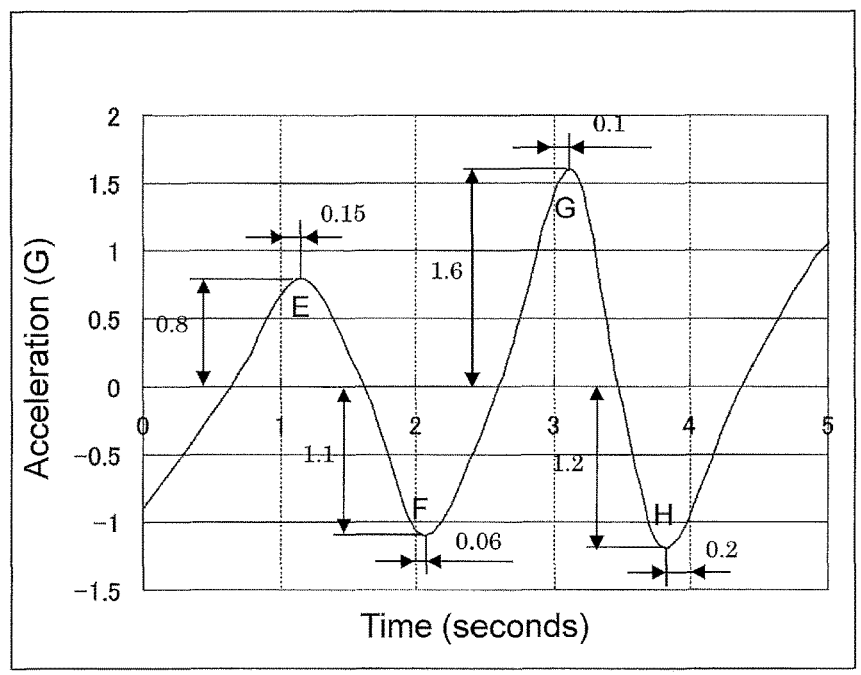

FIG. 10 is a flowchart of the shaking state determination operation. FIGS. 11a and 11b are graphs of acceleration sensed by the acceleration sensor 24 when the user shakes the device. In FIGS. 11a and 11b, the horizontal axis is time (seconds), and the vertical axis is acceleration (G).

In the determination of the shaking state, sounds are generated by the buzzer 22 to match the shaking period (S17). These sounds are generated once every second, for example.

The controller 18 detects the peaks of acceleration (the maximum and minimum values) on the basis of the sensing value from the acceleration sensor 24 (S31). In FIG. 11a, point A is sensed first.

Next, the controller 18 determines whether or not the sensed acceleration peak satisfies a first condition (S32). The first condition here is related to the clock time of the acceleration peak, and is a condition that the time when the acceleration reached the peak falls within a specific preset time range.

More precisely, in this embodiment the acceleration is set to peak in a shake once every second, for example, and the buzzer 22 generates a sound at the moment of this peak.

Specifically, in the graph in FIG. 11*a*, starting at zero seconds, the acceleration peaks at 1 second, two seconds, three seconds, and so forth, and a sound is emitted at each peak. The controller 18 then determines that the first condition is met when the acceleration peak produced when the user shakes the device is within a preset acceptable range of time (such as 0.15 second before or after). For example, the clock time at point A is 0.06 second before one second, and since this falls within 0.15 second before or after, which is the acceptable range in the example given here, the acceleration peak at point A is determined to satisfy the first condition.

The controller 18 then determines whether or not the sensed acceleration peak satisfies a second condition (S33). The second condition relates to the absolute value of acceleration. More precisely, in this embodiment the controller 18 determines that the second condition is met if the absolute value of acceleration at a peak is at or above a specific predetermined threshold (such as an acceleration of 1 G). For example, since the absolute value of acceleration at point A is 1.1 G, it is above the 1 G threshold in this example, and it is determined that the second condition is satisfied.

Consequently, the controller 18 this as one shake (S34).

S32 and S33 correspond to examples of a determination step.

The above operation is repeated until the number of shakes reaches a preset number (S35). In the graph shown in FIG. 11*a*, the peak of acceleration that is sensed next is point B, and the determination of S33 and S34 is carried out for the acceleration peak at point B. The clock time at point B is 0.1 second before two seconds, and the acceleration is −1.3 G. Therefore, the controller 18 also determines at point B that the first condition and second condition are met, and increases the number of shakes by one, giving a total of two shakes. The first and second conditions are also met at points C and D in FIG. 11*a*. Therefore, the controller 18 has a total of four shakes. S35 corresponds to an example of an end detection step.

Figure 12:
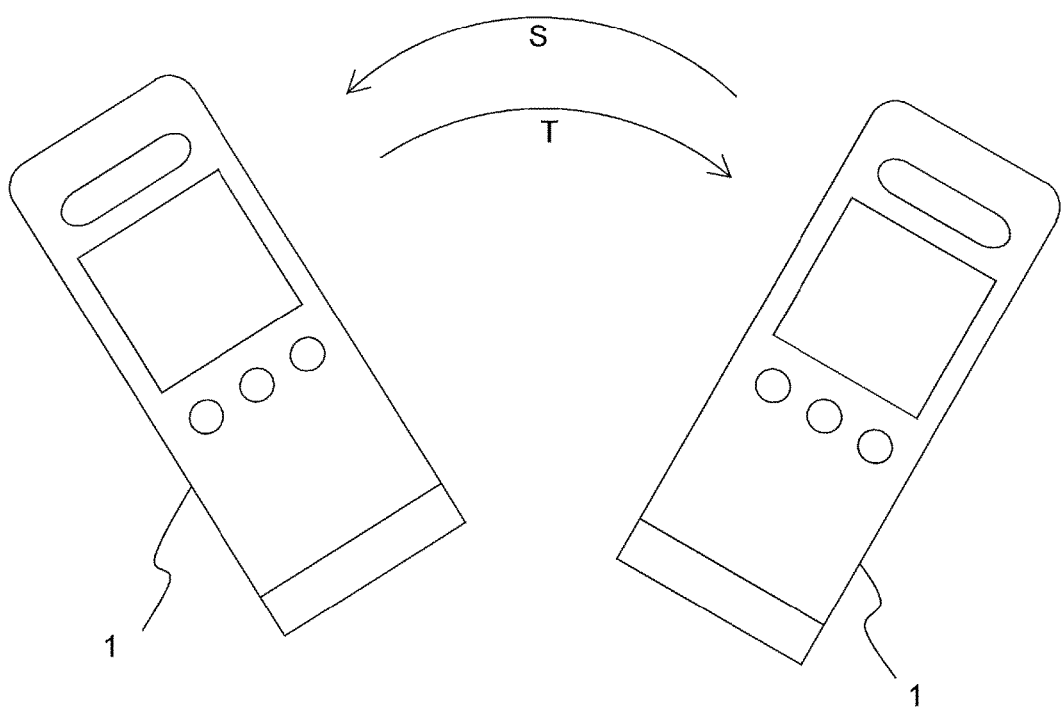
FIG. 12 is a diagram of an example of the shaking of the pharmaceutical injection device in FIG. 1.

One shake, in the example shown in FIG. 12, means that shaking the device from the right side to the left side (see the arrow S) is counted as one shake, and when the device is then shaken from the left side to the right side (see the arrow T), the number of shakes is counted as two. The sounds produced by the buzzer 22 are generated when approximately when the device reaches the right side shown in FIG. 12 and when it reaches the left side, that is, at both ends. Therefore, the user can perform the shaking properly by shaking the device according to the timing at which the buzzer 22 sounds at both ends. In other words, control is performed so that the buzzer 22 emits sounds so as to instruct the user when to shake the device.

Meanwhile, if no acceleration peak is detected (S31) even though the time limit is exceeded (S20), or if the first condition is not met (S32), or if the second condition is not met (S33), or if the operation is cancelled (S21), the control proceeds to S22.

As discussed above, the controller 18 counts a shake only when the first condition and the second condition are both met.

Next, this will be described further by using the graph in FIG. 11*b* as an example. In the graph shown in FIG. 11*b*, acceleration peaks are detected at points E, F, G, and H. The clock time at point E is 0.15 second after one second, and the first condition is met, but since the absolute value is 0.8 G, the second condition is not met. Therefore, even though an acceleration peak is detected at point E, no shake is counted. At points F and G, the first condition and second condition are both met, and one shake is counted at each. At point H, the time is 0.2 second before four seconds, and the first condition is not met, so no shake is counted. That is, in the graph shown in FIG. 11*b*, the number of shakes counted is two.

As discussed above, because the buzzer 22 emits sounds at specific intervals (the recommended shaking period; every second in Embodiment 1) to instruct the user to shake the device, the user can shake the device properly, and the pharmaceutical can be properly dissolved or mixed.

Also, because a shake is counted only when the first and second conditions are met, the user can perform the proper shaking the proper number of times, which allows the pharmaceutical to be dissolved or mixed more properly.

The air venting processing (S6) shown in FIG. 8 will now be described in detail.

Figure 13:
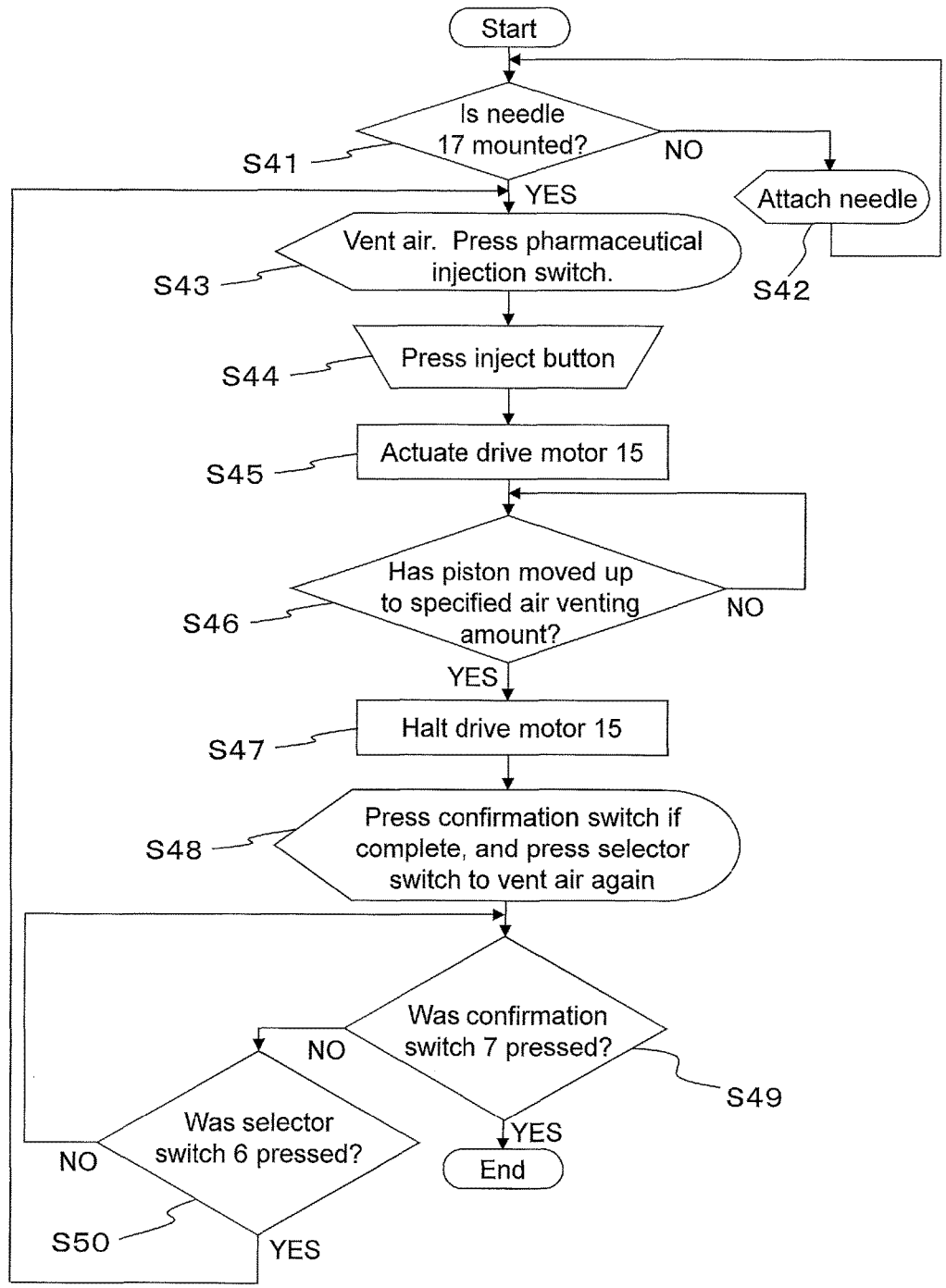
FIG. 13 is a flowchart of air venting processing in the pharmaceutical injection device in FIG. 1.

FIG. 13 is a flowchart of the operation in this air venting processing.

First, the controller 18 uses the needle detector switch 16 to check whether or not the needle 17 has been mounted to the needle mounting component 3 (S41). If it is determined that the needle 17 has not been mounted, the controller 18 causes the display component 5 to display "Attach needle" (S42).

If the needle 17 has been mounted, the controller 18 causes the display component 5 to display "Vent air. Press pharmaceutical injection switch" (S43).

Prompted by the display in S43, the user then presses the pharmaceutical injection switch 4 (S44).

When the pharmaceutical injection switch 4 is pressed, the controller 18 actuates the drive motor 15 to commence the air venting operation (S45).

Next, the controller 18 senses the amount of piston movement from the output of the encoder 15*b*, and advances the piston by a distance corresponding to the specified amount of air venting (S46).

When the piston 12 advances by the specified amount, the controller 18 then halts the drive motor 15 and ends the air venting operation (S47).

The controller 18 then causes the display component 5 to display "If finished, press confirmation switch. To vent again, press selector switch" (S48). Here, the user visually checks the state of air venting, and selects either to end the air venting operation or to perform the air venting operation again.

When the confirmation switch 7 is pressed, the air venting processing ends (S49).

On the other hand, if the selector switch 6 is pressed (S50), the control returns to S43 and the air venting operation is performed again.

In the above-mentioned air venting processing, the pharmaceutical injection switch is also used to start up the air venting operation, but if a separate air venting switch (not shown) is provided, then that switch is used instead. That is, in S44, the air venting switch would be pressed to start the drive motor in S45.

The pharmaceutical injection processing (S7) shown in FIG. 8 will now be described in detail.

Figure 14:
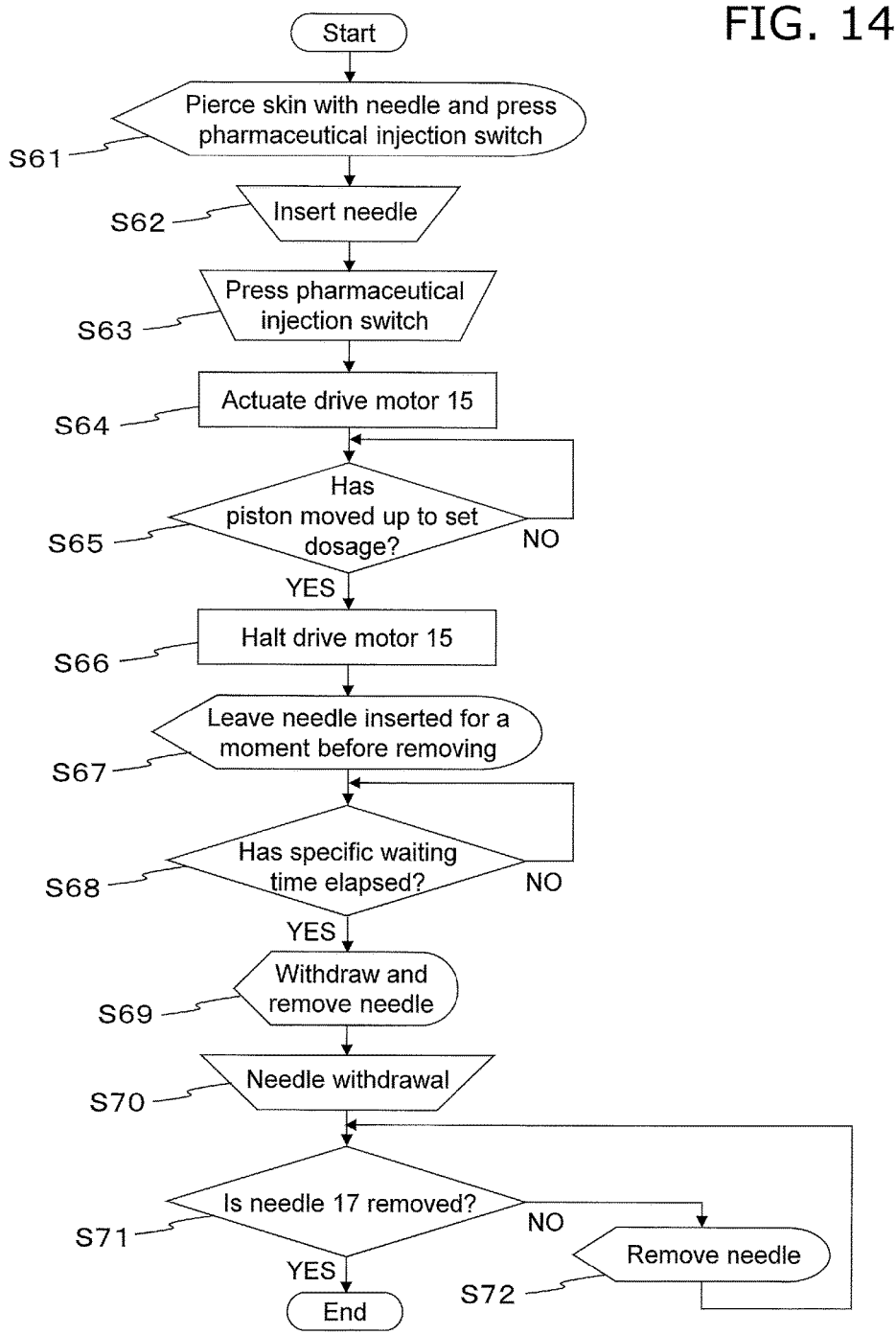
FIG. 14 is a flowchart of pharmaceutical injection processing in the pharmaceutical injection device in FIG. 1.

FIG. 14 is a flowchart of the operation in pharmaceutical injection processing.

First, the controller 18 causes the display component 5 to display "Inject. Stick needle in skin and press pharmaceutical injection switch" (S61). This prompts the user to stick in the needle and press the pharmaceutical injection switch 4.

When the user sticks the needle into his skin (S62) and presses the pharmaceutical injection switch 4 (S63), the controller 18 starts up the drive motor 15 (S64).

The controller 18 senses the amount of piston movement from the output of the encoder 15b, and advances the piston 12 by a distance corresponding to the specified amount of pharmaceutical injection (S65).

When the piston 12 advances by the specified amount, the controller 18 then halts the drive motor 15 (S66).

The controller 18 then causes the display component 5 to display "Leave needle inserted for a moment before removing," so that the user will keep the needle in its inserted state, without removing it, until all of the pharmaceutical has completed stopping coming out of the needle, even after the drive motor 15 has stopped (S67).

After waiting for a specific length of time (such as ten seconds) to elapse since the start of the display in S67 (S68), the controller 18 causes the display component 5 to display "Pull out needle" (S69). This prompts the user to remove the needle 17.

The user removes the needle 17 in response to the display on the display component 5 (S70).

When the needle detector switch 16 detects that the needle 17 has been removed, the controller 18 ends the pharmaceutical injection processing (S71). If the needle 17 has not been removed, the controller 18 causes the display component 5 to display "Remove needle" (S72).

As discussed above, the pharmaceutical injection device in this embodiment comprises the main case 1, the piston 12, the drive motor 15, the buzzer 22 (an example of an instruction signal generator), and the controller 18. The main case 1 has the cartridge holder 8. The piston 12 is inserted into the pharmaceutical cartridge 9 mounted to the cartridge holder 8. The drive motor 15 drives the piston 12. The buzzer 22 generates a sound (an example of an instruction signal) that instructs the user to shake the pharmaceutical cartridge 9 to mix or dissolve the pharmaceutical it contains. The controller 18 controls the buzzer 22 so as to emit sounds at specific intervals (that is, the recommended shaking period) to instruct the user to shake the device before operating the drive motor 15 and injecting the pharmaceutical.

As discussed above, the method for controlling a pharmaceutical injection device in this embodiment comprises S17 (an example of a shaking instruction step). In S17, sounds (an example of an instruction signal) that instruct the user to shake the pharmaceutical cartridge 9 in order to dissolve or mix the pharmaceutical it contains are emitted at specific intervals (that is, the recommended shaking period) to instruct the user to shake the device.

As discussed above, in this embodiment the controller 18 uses the buzzer 22 to generate sounds at specific intervals prior to pharmaceutical injection, so the pharmaceutical in the pharmaceutical cartridge 9 mounted to the cartridge holder 8 can be more properly mixed by shaking the main case 1 having the cartridge holder 8 according to these sounds from the buzzer 22.

Also, the instruction to shake properly can be given by sound to elderly people whose vision is not very acute.

Also, as discussed above, in this embodiment of a pharmaceutical injection device, when the pharmaceutical cartridge is replaced, a display to the effect that an instruction to dissolve or mix will be given, as shown in S15 in FIG. 9, prior to the pharmaceutical injection or the air venting operation.

This display will prompt the user to do the mixing or dissolving job.

As shown in S25 in FIG. 9, a display to the effect that an instruction to confirm the mixing state (the dissolution state) following the mixing operation will be issued is given after the holder lighting component 11 is lit.

This prompts the user to check the state of mixing or dissolution, and allows the user to properly carry out and check the mixing or dissolution.

Also, an instruction signal (such as a buzzer) is generated at specific intervals (the recommended shaking period) so that mixing or dissolution can be performed properly, and this facilitates the work done by the user.

In the following embodiments some of the ways for properly carrying out this mixing or dissolution.

In the above embodiment, the buzzer 22 merely emitting a beep or other such sound, as an example of the instruction signal generator, but a song, a melody, or other such sound that suits the user's tastes may be outputted from a sounder (not shown) or the like that outputs a melody, instead of using the above-mentioned buzzer 22.

The pharmaceutical injection device in Embodiment 2 pertaining to the present invention will now be described.

The pharmaceutical injection device in Embodiment 2 has basically the same configuration as Embodiment 1, but whereas sound (an auditory means) was used as an example of the instruction signal for instructing the user to shake the device in Embodiment 1, Embodiment 2 differs in that light (a visual means) is used. The description of Embodiment 2 below will focus on the differences from Embodiment 1. Those components that are the same as in Embodiment 1 will be numbered the same.

Figure 15:
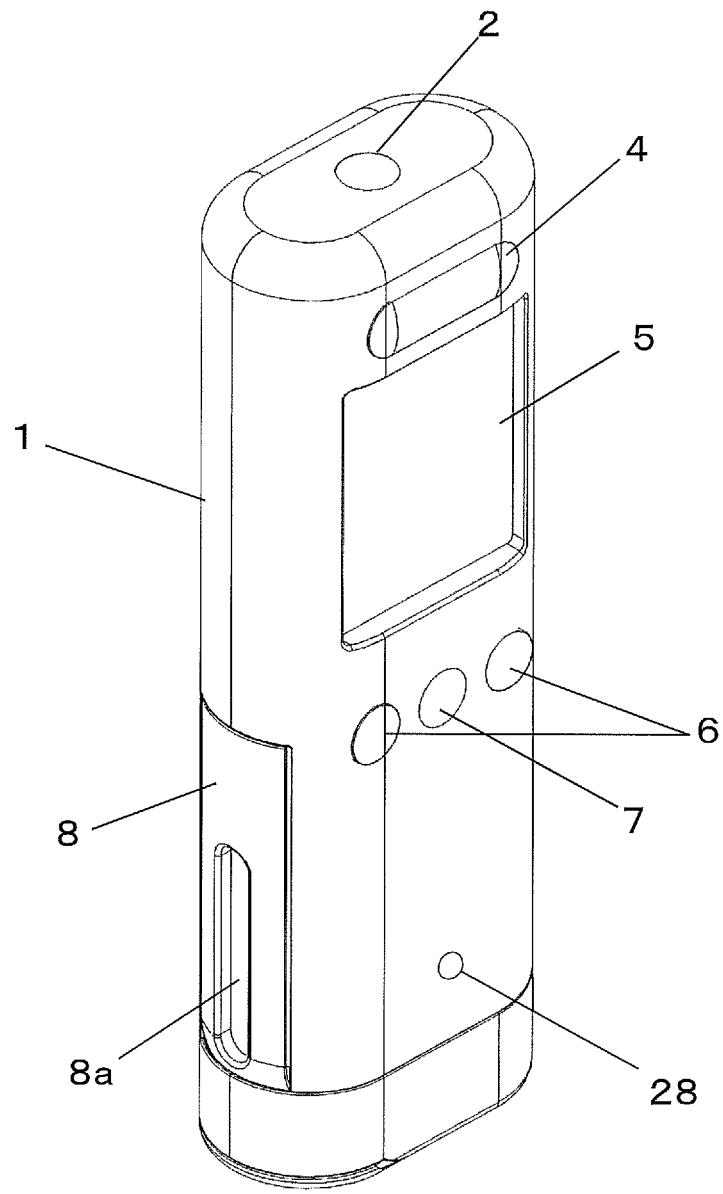
FIG. 15 is an oblique view of the pharmaceutical injection device in Embodiment 2 pertaining to the present invention.
Figure 16:
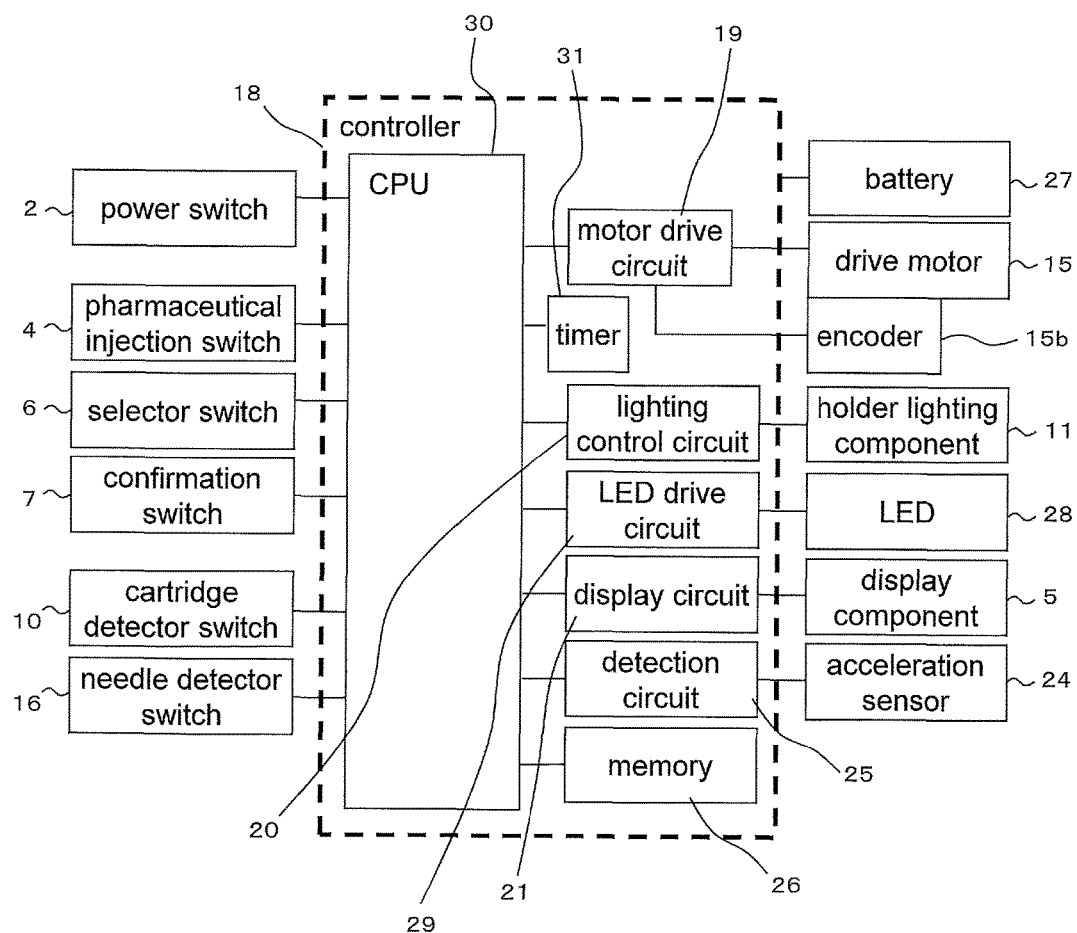
FIG. 16 is a block diagram of the configuration of the pharmaceutical injection device in FIG. 15.

FIG. 15 is an oblique view of the pharmaceutical injection device in Embodiment 2. FIG. 16 is a control block diagram of the pharmaceutical injection device in Embodiment 2.

As shown in FIG. 15, an LED (light emitting diode) 28 is provided under the confirmation switch 7 of the pharmaceutical injection device in Embodiment 2. As shown in FIG. 16, the LED 28 is connected to the CPU 30 via an LED drive circuit 29 inside the controller 18. In this embodiment, the buzzer 22 of Embodiment 1 is not provided.

Figure 17:
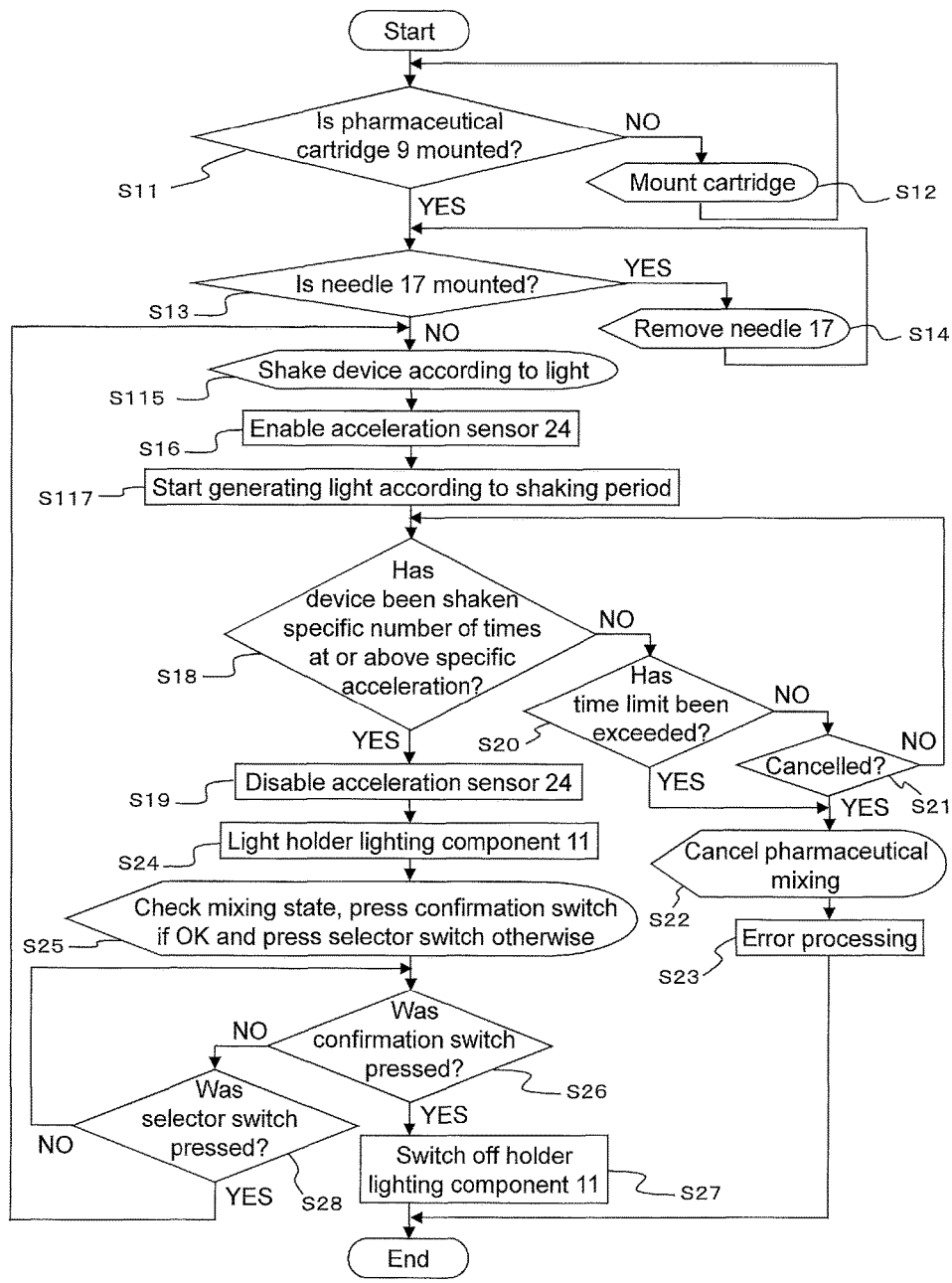
FIG. 17 is a flowchart of the pharmaceutical mixing processing in the pharmaceutical injection device in FIG. 1.

In Embodiment 2, the same control as in Embodiment 1 is performed, but the controller 18 generates light from the LED 28, instead of sound. FIG. 17 is a flowchart of the operation in pharmaceutical mixing processing in Embodiment 2.

As shown in FIG. 17, in Embodiment 2 steps S115 and S117 are provided instead of S15 and S17 shown in FIG. 9. Specifically, in S13, after it has been confirmed that no needle has been mounted, the controller 18 causes the display component 5 to display "Shake device according to light."

Then, after the acceleration sensor 24 is enabled in S16, the controller 18 controls the LED 28 to flash the light at specific intervals (S117). Specifically, light is generated at points of after one second, after two seconds, after three seconds, after four seconds, and so on as shown in FIGS. 11a and 11b.

The user can perform the proper shaking as instructed by the light generated by the LED 28.

As discussed above, the pharmaceutical injection device in this embodiment comprises the main case 1, the piston 12, the drive motor 15, the LED 28 (an example of an instruction signal generator), and the controller 18. The main case 1 has the cartridge holder 8. The piston 12 is inserted into the pharmaceutical cartridge 9 mounted to the cartridge holder 8. The drive motor 15 drives the piston 12. The LED 28 generates light (an example of an instruction signal) that instructs the user to shake the pharmaceutical cartridge 9 to mix or dissolve the pharmaceutical it contains. The controller 18 controls the LED 28 via the LED drive circuit 29 so as to emit light at specific intervals (that is, the recommended shaking period), such as at intervals of one second, to instruct the user to shake the device before operating the drive motor 15 and injecting the pharmaceutical.

Also, as discussed above, the method for controlling a pharmaceutical injection device in this embodiment comprises the step S117 (an example of a shaking instruction step). In S117, light (an example of an instruction signal) that instructs the user to shake the pharmaceutical cartridge 9 to dissolve or mix the pharmaceutical it contains is emitted at specific intervals (that is, the recommended shaking period) to instruct the user to shake the device.

As discussed above, in this embodiment the configuration is such the controller 18 causes the LED 28 to flash at specific intervals prior to pharmaceutical injection, and the main case 1 is shaken according to the flashing of this LED 28, so the pharmaceutical in the pharmaceutical cartridge 9 held in the cartridge holder 8 can be more properly mixed.

Also, the instruction to shake properly can be given by light to elderly people whose hearing is not very acute.

In Embodiment 2 above, an example is given in which the LED 28 is provided on the outside of the main case 1, and light from the LED 28 is used as an instruction signal to instruct the user to shake the device, but if the LED 28 is not provided, light emitted by the holder lighting component 11 may be used as this instruction signal.

In this case, the controller 18 starts flashing the holder lighting component 11 in S117 shown in FIG. 17, determines that the dissolution or mixing is complete when a specific number of shaking is reached, then halts the flashing of the holder lighting component 11, and lights the holder lighting component 11 in S24. The holder lighting component 11 here corresponds to an example of an instruction signal generator. The LED 28 does not have to be provided.

By thus using a configuration in which an instruction for optimizing the mixing state of the pharmaceutical is executed by flashing the holder lighting component 11 of the cartridge holder 8, the configuration of the pharmaceutical injection device can be simplified.

Also, since controller 18 flashes the holder lighting component 11 of the cartridge holder 8 at specific intervals prior to pharmaceutical injection, the pharmaceutical in the pharmaceutical cartridge 9 held in the cartridge holder 8 can be more properly mixed by shaking the main case 1 according to the flashing of the holder lighting component 11.

In Embodiment 2 above, only light is generated by the LED 28 at specific interval, and in Embodiment 1 above, only sound is generated by the buzzer 22 at specific intervals, and a manual mixing operation (an operation in which the main case 1 is shaken) is performed, but the LED 28 and the buzzer 22 may both be provided at the same time, and controlled so that light and sound are generated at the same time. The control block to which the LED 28 and the buzzer 22 are provided may be the same as in FIG. 18 (discussed below).

Specifically, the buzzer 22 can output buzzer sounds such as "beep beep" in synchronization with the flashing of the LED 28 (that is, the recommended shaking period), according to the flashing of the LED 28 at specific intervals, which allows the main case 1 to be shaken more accurately.

This control is compatible with both users with poor hearing and users with poor vision.

Furthermore, if a song, melody, or other such sound that suits the tastes of the user is outputted by a sounder (not shown) or the like that outputs a melody instead of the buzzer 22, this can be used in conjunction with the LED 28 to perform the manual mixing operation more rhythmically and more accurately.

In this case, the melody, song, speech, or the like is stored ahead of time as audio data (sound data) in the memory 26, and a pre-selected melody or the like is outputted from the above-mentioned sounder in synchronization with the flashing of the LED 28. This synchronization of the flashing of the LED 28 and the buzzer or sounder can be accomplished by a control method involving the software (program) of the controller 18, or by a hardware control method involving a separate synchronization circuit (not shown).

When light and sound are thus generated in synchronization, the holder lighting component 11 may be used in place of the LED 28.

Thus combining the visual guidance of the LED 28 with the auditory guidance of the buzzer 22 provides a pharmaceutical injection device that is user-friendly and optimizes the mixing state.

In Embodiment 1 above, sound is used as an example of an instruction signal, and in Embodiment 2 above, light is used as an example of an instruction signal, but vibration may be used instead of these. In this case, a vibrator is electrically connected to the controller 18, and vibrations are emitted at specific intervals instead of light or sound.

Also, light, sound, and vibration may all be emitted at the same as instruction signals.

Also, in Embodiment 2, only one LED 28 is provided, but two more may be provided. For example, two may be disposed side by side in the left and right direction in FIG. 15, and controlled so that they are alternately lit on the left and right. In this case, the user shakes the device to the right when the right LED lights, and shakes the device to the left when the left LED lights, allowing the device to be shaken according to the flashing of the left and right LEDs, and this affords better mixing.

Furthermore, when the holder lighting component 11 is used instead of the LED 28, the lights 11a and 11b of the holder lighting component 11 may be controlled so that they light alternately.

Next, Embodiment 3 of the present invention will be described. The basic configuration of the pharmaceutical injection device in Embodiment 3 is the same as that in Embodiment 2, but in Embodiment 3 light is used as an instruction signal for instructing the user to shake the device, and sound produced by the buzzer 22 used in Embodiment 1 is used as a confirmation signal that confirms to the user whether or not the device has been properly shaken. Accordingly, the description will focus on these differences. Components that are the same as those in Embodiments 1 and 2 will be numbered the same.

Figure 18:
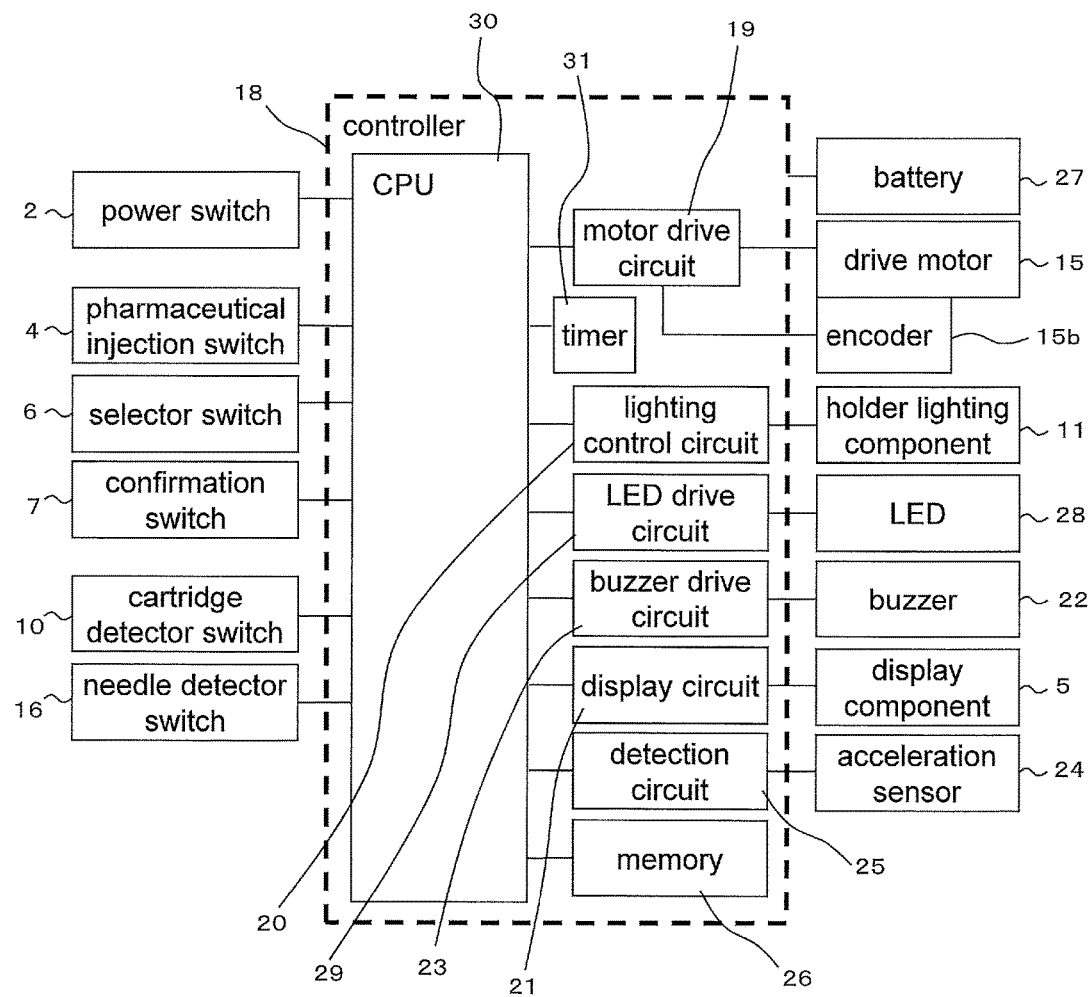
FIG. 18 is a block diagram of the configuration of the pharmaceutical injection device in Embodiment 3 pertaining to the present invention.

The external configuration of the pharmaceutical injection device in Embodiment 3 is the same as that shown in FIG. 15 for Embodiment 2. FIG. 18 shows the control blocks of the pharmaceutical injection device in Embodiment 3. As shown in FIG. 18, the pharmaceutical injection device in Embodiment 3 differs from Embodiment 2 in that is comprises the buzzer 22. As described for Embodiment 1, this buzzer 22 is electrically connected to the CPU 30 via the buzzer drive circuit 23 inside the controller 18.

Figure 19:
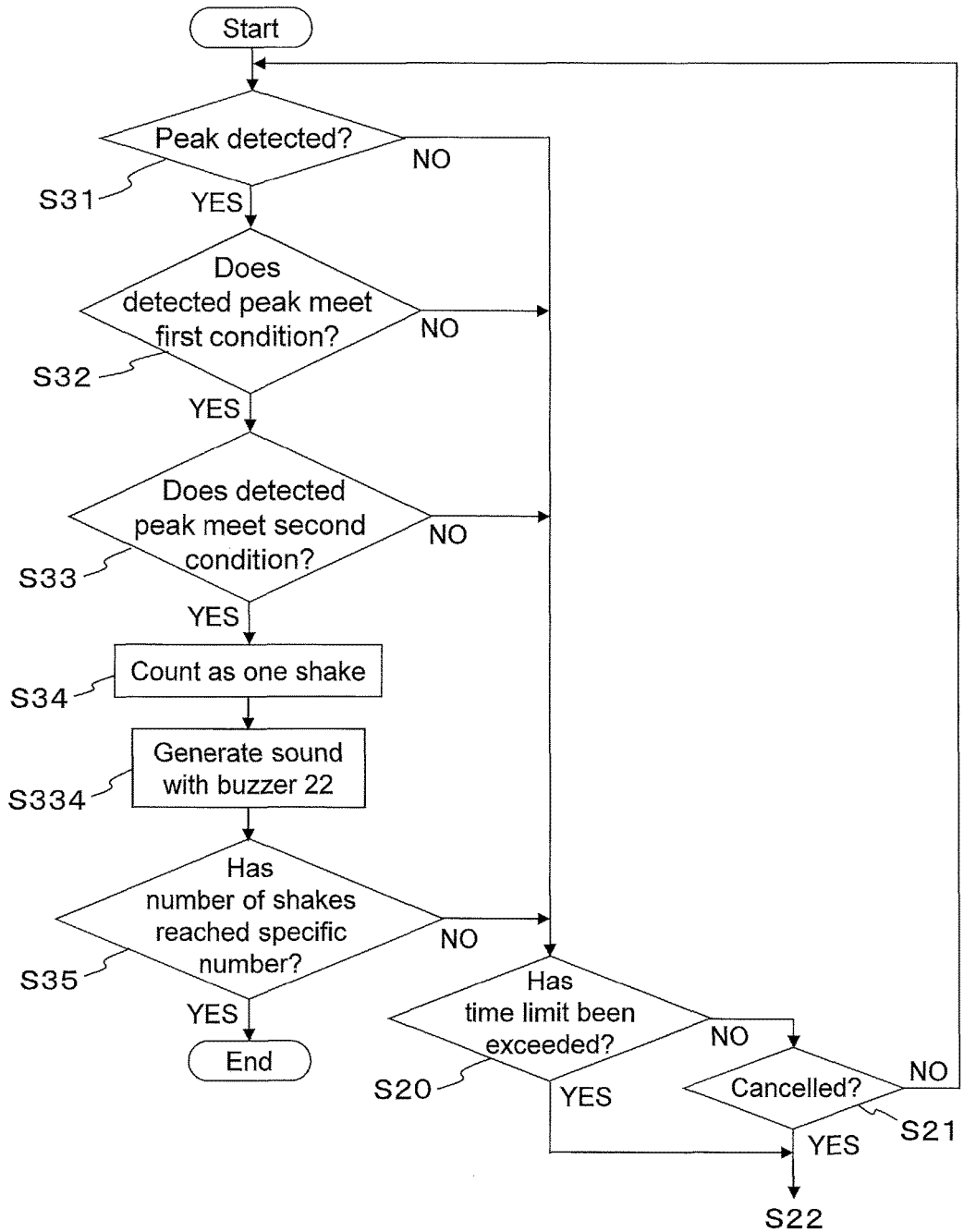
FIG. 19 is a flowchart of the shaking determination operation in the pharmaceutical injection device in FIG. 18.

FIG. 19 is a flowchart of the operation for determining the shaking state in a method for controlling the pharmaceutical injection device in Embodiment 3.

In S117 shown in FIG. 17, the operation shown in FIG. 19 to determine the shaking state is performed when the light flashes at specific intervals according to the shaking period. Just as in Embodiments 1 and 2, the controller 18 senses the peak of acceleration, and determines whether the sensed acceleration peak satisfies first and second conditions (S31, S32, and S33). If the first and second conditions are met, the controller 18 counts this as one shake.

The controller 18 then controls the buzzer 22 to generate a sound (S334). This S334 corresponds to an example of a notification step.

When the number of shakes reaches a specific number, the pharmaceutical mixing processing ends.

Specifically, in Embodiment 3, the LED 28 is flashed at specific intervals, and the buzzer 22 generates a sound when proper shaking has been performed that satisfies the first and second conditions.

Consequently, the user can confirm whether or not the shaking operation is performed properly according to the LED 28.

As discussed above, the pharmaceutical injection device in Embodiment 3 comprises the main case 1, the piston 12, the drive motor 15, the LED 28 (an example of an instruction signal generator), the buzzer 22 (an example of a confirmation signal generator), the acceleration sensor 24, and the controller 18. The main case 1 has the cartridge holder 8. The piston 12 is inserted into the pharmaceutical cartridge 9 mounted to the cartridge holder 8. The drive motor 15 drives the piston 12. The LED 28 generates light (an example of an instruction signal) that instructs the user to shake the pharmaceutical cartridge 9 to mix or dissolve the pharmaceutical it contains. The buzzer 22 generates a sound (an example of a confirmation signal) that confirms to the user whether or not the shaking is proper for mixing or dissolving the pharmaceutical in the pharmaceutical cartridge 9. The acceleration sensor 24 senses the acceleration of the main case 1. The controller 18 controls the LED 28 so as to emit light at specific intervals (the recommended shaking period) to instruct the user to shake the device before operating the drive motor 15 and injecting the pharmaceutical. The controller 18 also controls the buzzer 22 so as to generate a sound when the shaking is performed properly, on the basis of the sensing value of the acceleration sensor.

Also, the method for controlling the pharmaceutical injection device in this embodiment comprises S117 (see FIG. 17), which is an example of a shaking instruction step, S32 and S33, which are examples of a determination step, and S334, which is an example of a notification step (see FIG. 19).

In S117, lights (an example of an instruction signal) that instruct the user to shake the pharmaceutical cartridge 9 to dissolve or mix the pharmaceutical it contains are emitted at specific interval so as to instruct the user to do this shaking. S32 and S33 involve determining whether or not the shaking instructed by S117 is the specified shaking operation. S334 involves notifying the user that it has been determined to be the specified shaking operation.

Thus, in Embodiment 3, the LED 28 is flashed at specific intervals, and the buzzer 22 is used to generate sounds when the controller 18 determines that the shaking operation is proper.

The control discussed above allows the user to recognize that the shaking the user is doing is the proper operation by hearing the sound, and also allows the shaking to be performed according to the light.

Also, although there is a certain amount of time lag, it is easy to recognize the proper shaking timing since the instructions are generated on the right and left sides shown in FIG. 12.

In Embodiment 3 above, light from the LED 28 is used as an example of an instruction signal that instructs the user to shake the pharmaceutical cartridge 9 to dissolve or mix the pharmaceutical it contains, and the sound of the buzzer 22 is used as a confirmation signal to confirm whether or not the proper shaking is done to mix or dissolve the pharmaceutical in the pharmaceutical cartridge 9, but this may also be reversed. Specifically, the sound of the buzzer 22 may be used as an example of an instruction signal, and the light from the LED 28 may be used as an example of a confirmation signal.

In this case, the buzzer 22 serving as the instruction signal emits a beeping sound at specific intervals (the shaking period). The LED 28 serving as the confirmation signal flashes if the shaking is proper, but does not shake otherwise.

Consequently, the user can recognize that the shaking is improper because the LED 28 is not flashing.

Apart from this, it is also possible for the LED 28 serving as the confirmation signal to be a multicolor (RGB) type of LED, in which case the light flashes green or blue if the shaking is proper, and flashes red or orange otherwise. This allows the user to visually recognize the shaking state.

Also, if the shaking is improper, the sound of the buzzer 22 may be some sound that is different from the usual, such as a buzz.

Furthermore, the instruction signal or the confirmation signal may consist of vibration. When vibration is used, a vibrator should provided that is electrically connected to the controller 18. A combination of light, sound, and vibration may also be suitably used for the combination of instruction signal and confirmation signal.

Also, two of light, sound, and vibration may be used as the instruction signal, and the remaining one used as a confirmation signal, or the other way around.

Also, in Embodiment 3, the LED 28 is used as an example of an instruction signal generator for generating an instruction signal, and the buzzer 22 is used as an example of a confirmation signal generator for generating a confirmation signal, but either the buzzer 22 or the LED 28 may be used as an instruction signal generator that doubles as a confirmation signal generator.

For example, when just the buzzer 22 is used without using the LED 28, an example of the instruction signal is a beep sound, and an example of a confirmation signal is to change this sound to a buzz sound.

Specifically, the user can confirm that he is properly shaking the device when the sound changes to a buzz after he starts shaking the device according to the "beep, beep, beep" sounds and the shaking is deemed to meet the first and second conditions. When a confirmation signal such as this is used, the pitch or volume of the sound may be changed from that of the sound when used as an example of an instruction signal.

On the other hand, when just the LED 28 is used, without using the buzzer 22, the color or intensity of the light when it is used as an example of an instruction signal may be changed from that when it is used as an example of a confirmation signal.

In Embodiment 3, the light of the LED 28 is used as an example of an instruction signal that instructs the user to shake the pharmaceutical cartridge 9 to dissolve or mix the pharmaceutical it contains, and the sound of the buzzer 22 is used as a confirmation signal to confirm whether or not the proper shaking is done to mix or dissolve the pharmaceutical in the pharmaceutical cartridge 9, but just a confirmation signal may be used, without using any instruction signal.

In this case, the display in S115 will be only a display of "Shake device," and since it is hard to tell when to start the shaking, the buzzer 22 may be controlled so as to emit a louder sound than normal, for example.

In Embodiments 1 to 3, the controller 18 generated light or sound with the LED 28 or the buzzer 22 as an example of the instruction signal generator, until the number of times the main case 1 is shaken (sensed by the acceleration sensor 24) reached a specific number, but this control is not the only option. For example, after the buzzer 22 generates its sound (S17 in FIG. 9) in Embodiment 1, sound may be generated at specific intervals and for a specific length of time, and the sound then stopped after the specific length of time has elapsed. The same control may be performed for the LED 28 in Embodiments 2 and 3.

In this case, since the acceleration sensor 24 is not used in Embodiments 1 and 2, the acceleration sensor 24 need not be provided.

Thus, there is also a situation in which the configuration is such that light or sound is generated for a specific length of time by the LED 28 or the buzzer 22, and if the main case 1 is shaken during that time, the pharmaceutical in the pharmaceutical cartridge 9 will be properly mixed.

In Embodiments 1 to 3 above, the shaking is determined to be proper when the first and second conditions are met, but the shaking may instead be determined to be proper when only the first condition or the second condition is met.

Also, the threshold for the absolute value of acceleration at peak and the range of clock time at which the acceleration peaks in Embodiments 1 to 3 above are just examples, and may be varied as needed. Specifically, depending on the type of pharmaceutical, there may be situations in which mixing or dissolution will be better if the device is shaken slowly, so the numerical values for the first and second conditions may be changed as needed according to the type of pharmaceutical.

In Embodiments 1 to 3 above, the user is given an instruction by displaying an instruction message on the display component 5, but instructions may also be given to the user in other ways. For instance, the user can be given an instruction by installing a speech output device and converting the instruction message into speech. In Embodiments 1 and 3, the configuration may be such that a speech output device is provided instead of the buzzer 22.

In this case, more detailed manual operation guidance can be provided, such as giving the instruction to start manual mixing as "start" in speech, or telling the user "five more times" by speech during the shaking, or saying "You're finished" at the end, accommodating a wide variety of situations.

In Embodiments 1 to 3, the needle mounting component 3 is connected to the cartridge holder 8 of the main case 1 as shown in FIG. 3, for example, but this is not the only option, and this component may be connected to the distal end portion of the pharmaceutical cartridge 9.

In the above description, the LED 28 is used for guidance in the manual mixing operation, and the holder lighting component 11 is used to confirm the mixing state, but the LED 28 and the holder lighting component 11 can also be used to indicate the timing at which the needle should be removed from the skin after the pharmaceutical has been injected with the pharmaceutical injection device.

More specifically, once the dissolution or mixing of the pharmaceutical in the pharmaceutical cartridge 9 is finished, air bubbles are vented from the needle, and then the needle 17 is inserted into the skin and pharmaceutical injection is performed automatically by the drive motor 15 that drives the piston 12 used for injection.

Once a specific amount of time has passed since this injection of the pharmaceutical is finished (S68 in FIG. 14), the LED 28 or the holder lighting component 11 is flashed. The user checks the flashing of the LED 28 or the holder lighting component 11 and pulls the needle out of his skin (that is, moves the main case 1 of the pharmaceutical injection device away from the skin) (S70).

When the buzzer 22 is provided as in the pharmaceutical injection device in Embodiments 1 and 3, the user may be notified by switching on the buzzer 22 in conjunction with the start of the flashing of the LED 28 or the holder lighting component 11.

Also, the user can be notified to change the color during injection and the color when it is alright to remove the needle from the skin (such as from red to green) by utilizing an LED or the like that can light in a plurality of colors for the LED 28 or the holder lighting component 11.

In Embodiments 1 to 3, the controller 18 determined whether or not any pharmaceutical is remaining in S2, but this is not the only option. For example, the following control may be employed. A display prompting the user to check the remaining amount of pharmaceutical is given on the display component 5 in S2, and when the user operates the confirmation switch 7, the control moves to S3. Again in S3, a display instructing the user to check whether the pharmaceutical is within its expiration date is given, and when the user operates the confirmation switch 7, the control moves to S3.

Thus, the control may be such that the user is instructed to make a check.

Some or all of the various processing, steps (S), and so forth in the method for controlling the pharmaceutical injection device in Embodiments 1 to 3 above may be realized using a program, for example. Also, some or all of the various processing, steps (S), and so forth in the method for controlling the pharmaceutical injection device in Embodiments 1 to 3 above may be performed by the CPU (central processing unit) of a computer. The above-mentioned program operates in conjunction with the computer.

Another way in which the above-mentioned program may be used is to record it to a ROM or other such recording medium that can be read by a computer. Yet another way to use a program is to transfer it over the Internet or another such transfer medium, or through light, radio waves, or another such transfer medium, to be read by a computer. For example, the pharmaceutical injection device in the above embodiments may be connected to a computer by USB or the like, and a program for executing an information reading method may be transferred over the Internet. This computer is not limited to a CPU and other such hardware, and may instead be firmware or an OS. Also, some or all of the various processing, steps, and so forth in the information reading method in the embodiments may be realized with hardware, or may be realized with software. They may also be realized with processing that combines software and hardware.

INDUSTRIAL APPLICABILITY

Certain embodiments relate to a pharmaceutical injection device and the method for controlling a pharmaceutical injection device. Certain embodiments have the effect of making it possible for a pharmaceutical to be dissolved or mixed more properly, and the inventors anticipate application as a pharmaceutical injection device that injects insulin, growth hormone, or other such pharmaceuticals.

The invention claimed is:

1. A pharmaceutical injection device, comprising:
a main case that has a cartridge holder configured to hold a pharmaceutical cartridge;
a piston that is inserted into the pharmaceutical cartridge mounted to the cartridge holder;
a drive motor that drives the piston;
an instruction signal generator that generates an instruction signal that instructs a user to shake the pharmaceutical cartridge to mix or dissolve a pharmaceutical that is contained in the pharmaceutical cartridge; and
a controller that controls the instruction signal generator so as to issue the instruction signal at specific intervals to give an instruction to shake the pharmaceutical cartridge for properly mixing or dissolving a pharmaceutical before the drive motor is actuated to inject the pharmaceutical, and
wherein the instruction signal generator generates an instruction signal of light and/or sound and/or vibration at the specific intervals for a shaking period.

2. The pharmaceutical injection device according to claim 1, further comprising:
a confirmation signal generator that generates a confirmation signal that confirms whether or not the pharmaceutical in the pharmaceutical cartridge has been properly shaken for mixing or dissolution; and
an acceleration sensor that senses an acceleration value of the main case,
wherein the controller controls the confirmation signal generator so as to generate the confirmation signal when the shaking is determined to have been properly performed on a basis of the acceleration value of the acceleration sensor.

3. The pharmaceutical injection device according to claim 2,
wherein the confirmation signal generator generates an instruction signal of light and/or sound.

4. The pharmaceutical injection device according to claim 2,
wherein the controller controls the confirmation signal generator so as to generate the confirmation signal when the acceleration value sensed by the acceleration sensor is at or above a preset threshold.

5. The pharmaceutical injection device according to claim 4,
wherein the controller controls the confirmation signal generator so as to generate the confirmation signal when the acceleration value sensed by the acceleration sensor is at or above a preset threshold and a clock time at which the acceleration value reaches its peak is within a specific, preset range of time.

6. The pharmaceutical injection device according to claim 2,
wherein the instruction signal generator also serves as the confirmation signal generator, and
the controller controls the instruction signal generator so as to update the instruction signal and generate the confirmation signal when the acceleration value sensed by the acceleration sensor is at or above a preset threshold.

7. The pharmaceutical injection device according to claim 6,
wherein the controller controls the instruction signal generator so as to update the instruction signal and generate the confirmation signal when the acceleration value sensed by the acceleration sensor is at or above a preset threshold and a clock time at which the acceleration value reaches its peak is within a specific, preset range of time.

8. The pharmaceutical injection device according to claim 6,
wherein the instruction signal is sound or light, and
the controller generates the confirmation signal, varying a pitch or volume of the sound, or a color or intensity of the light.

9. The pharmaceutical injection device according to claim 1,
further comprising an acceleration sensor that senses an acceleration value of the main case,
wherein the controller controls the instruction signal generator so as to halt the instruction signal once a number of shakes sensed by the acceleration sensor reaches a specific number.

10. The pharmaceutical injection device according to claim 9,
wherein the controller counts it as a shake when the acceleration value sensed by the acceleration sensor is at or above a preset threshold.

11. The pharmaceutical injection device according to claim 10,
wherein the controller counts it as a shake when the acceleration value sensed by the acceleration sensor is at or above a preset threshold and a clock time at which the acceleration value reaches its peak is within a specific, preset range of time.

12. The pharmaceutical injection device according to claim 1,
wherein the controller controls the instruction signal generator so as to generate the instruction signal for a specific length of time.

13. The pharmaceutical injection device according to claim 1,
further comprising a display component that is connected to the main case,
wherein the controller causes the display component to display an instruction to shake the main case before the instruction signal is generated.

14. The pharmaceutical injection device according to claim 1,
further comprising a cartridge detector that is connected to the cartridge holder and detects whether or not there is a pharmaceutical cartridge,
wherein the instruction signal generator generates the instruction signal after a mounting of the pharmaceutical cartridge to the cartridge holder has been detected by the cartridge detector.

15. The pharmaceutical injection device according to claim 14,
further comprising a display component that is connected to the main case,
wherein the controller causes the display component to display an instruction to shake the main case after the mounting of the pharmaceutical cartridge to the cartridge holder has been detected.

16. The pharmaceutical injection device according to claim 1,
further comprising:
a needle mounting component for mounting a needle that injects the pharmaceutical in the pharmaceutical cartridge into a body;
a needle detector that detects the mounting of the needle to the needle mounting component; and
a display component that is connected to the main case,
wherein, before the shake instruction signal is generated, the controller causes the display component to display an instruction to remove the needle from the needle mounting component if the needle detector has detected the mounting of a needle to the needle mounting component.

17. The pharmaceutical injection device according to claim 1,
further comprising a holder lighting component that illuminates the cartridge holder,
wherein the controller lights the holder lighting component after the instruction signal has been halted.

18. The pharmaceutical injection device according to claim 17,
further comprising a display component that is connected to the main case,
wherein the controller causes the display component to display an instruction to confirm the mixing or dissolution state after the holder lighting component has been lit.

19. The pharmaceutical injection device according to claim 17,
wherein the holder lighting component also serves as the instruction signal generator, and
the controller flashes the holder lighting component at specific intervals.

20. The pharmaceutical injection device according to claim 1,
wherein the controller controls the instruction signal generator so as to stop issuing the instruction signal at specific intervals when a specific number of shakes has been reached.

* * * * *